(12) United States Patent
Vadivelu

(10) Patent No.: US 10,549,055 B2
(45) Date of Patent: *Feb. 4, 2020

(54) MEDICAL APPARATUS WITH HYPOPHARYNGEAL SUCTIONING CAPABILITY

(71) Applicant: AIRGUARD, LLC, Fairfield, CT (US)

(72) Inventor: Nalini Vadivelu, Fairfield, CT (US)

(73) Assignee: AIRGUARD, LLC, Fairfield, CT (US)

( * ) Notice: Subject to any disclaimer, the term of this patent is extended or adjusted under 35 U.S.C. 154(b) by 877 days.

This patent is subject to a terminal disclaimer.

(21) Appl. No.: 15/023,371

(22) PCT Filed: Sep. 23, 2014

(86) PCT No.: PCT/US2014/057059
§ 371 (c)(1),
(2) Date: Mar. 19, 2016

(87) PCT Pub. No.: WO2015/042607
PCT Pub. Date: Mar. 26, 2015

(65) Prior Publication Data
US 2016/0206841 A1  Jul. 21, 2016

Related U.S. Application Data

(60) Continuation-in-part of application No. 13/359,473, filed on Jan. 26, 2012, now Pat. No. 9,687,622, which
(Continued)

(51) Int. Cl.
*A61M 16/04* (2006.01)
*A61J 15/00* (2006.01)

(52) U.S. Cl.
CPC ...... *A61M 16/0463* (2013.01); *A61M 16/047* (2013.01); *A61M 16/0409* (2014.02);
(Continued)

(58) Field of Classification Search
CPC ............. A61M 16/00; A61M 16/0463; A61M 16/0415; A61M 16/0409; A61M 16/047;
(Continued)

(56) References Cited

U.S. PATENT DOCUMENTS

| 6,439,232 B1 * | 8/2002 | Brain | A61M 16/04 128/200.26 |
| 2006/0162730 A1 * | 7/2006 | Glassenberg | A61B 1/267 128/207.14 |

(Continued)

*Primary Examiner* — Tu A Vo
(74) *Attorney, Agent, or Firm* — Raymond A. Nuzzo

(57) ABSTRACT

A laryngeal mask apparatus to ventilate a patient and also suck in fluids and secretions in the patient's hypopharyngeal region. The laryngeal mask apparatus has a mask, a flexible breathing tube in communication with the mask and a suction tube which has a plurality of suctioning ports that face the back of the patient's throat when the mask is inserted into the patient's throat. When suction is created within the suction tube, fluids and secretions in the patient's hypopharyngeal region are sucked into the plurality of suction ports. The laryngeal mask apparatus also has a flexible air capillary tube positioned within the interior of the suction tube to provide an air flow that decreases the direct suction forces on the mucosa of the patient's throat that are caused by the suction of the plurality of suction ports.

6 Claims, 25 Drawing Sheets

Related U.S. Application Data is a division of application No. 11/817,606, filed as application No. PCT/US2006/010623 on Mar. 23, 2006, now Pat. No. 8,105,316.

(60) Provisional application No. 60/665,585, filed on Mar. 25, 2005, provisional application No. 61/881,157, filed on Sep. 23, 2013, provisional application No. 61/881,775, filed on Sep. 24, 2013.

(52) U.S. Cl.
CPC ...... *A61M 16/0415* (2014.02); *A61J 15/0003* (2013.01); *A61J 15/0049* (2013.01); *A61J 15/0073* (2013.01)

(58) Field of Classification Search
CPC .............. A61M 16/04; A61M 16/0402; A61M 2210/1028; A61M 16/0434; A61M 1/00; A61M 27/00; A61M 15/14; A61M 5/00; A61M 5/315; A61M 37/00; A61M 29/00; A61J 15/0073; A61J 15/0003; A61J 15/0049; A61F 5/44; A61F 2/00; A61F 2/02

See application file for complete search history.

(56) References Cited

U.S. PATENT DOCUMENTS

| | | | |
|---|---|---|---|
| 2006/0180156 A1* | 8/2006 | Baska | A61M 16/04 128/207.15 |
| 2008/0071249 A1* | 3/2008 | Vadivelu | A61M 16/0463 604/540 |
| 2010/0307508 A1* | 12/2010 | Li | A61M 16/0463 128/207.15 |
| 2013/0112207 A1* | 5/2013 | Roth | A61M 16/04 128/207.15 |
| 2013/0220332 A1* | 8/2013 | Baska | A61M 16/04 128/207.15 |

* cited by examiner

MEDICAL APPARATUS WITH HYPOPHARYNGEAL SUCTIONING CAPABILITY

CROSS-REFERENCE TO RELATED APPLICATIONS

This application claims the benefit of U.S. provisional application No. 61/881,157, filed Sep. 23, 2013. The entire disclosure of U.S. provisional application No. 61/881,157 is hereby incorporated by reference. This application also claims the benefit of U.S. provisional application No. 61/881,775, filed Sep. 24, 2013. The entire disclosure of U.S. provisional application No. 61/881,775 is hereby incorporated by reference.

This application is also a continuation-in-part of U.S. application Ser. No. 13/359,473, filed Jan. 26, 2012, which is a divisional application of U.S. application Ser. No. 11/817,606, filed Mar. 23, 2006, now U.S. Pat. No. 8,105,316, which is the National Stage of international application no. PCT/US2006/010623, filed Mar. 23, 2006, which claims the benefit of U.S. provisional application No. 60/665,585, filed Mar. 25, 2005. The entire disclosures of application Ser. Nos. 13/359,473, 11/817,606, PCT/US2006/010623 and No. 60/665,585 are hereby incorporated by reference. The entire disclosure of U.S. Pat. No. 8,105,316 is hereby incorporated by reference.

TECHNICAL FIELD

The present invention generally relates to nasogastric tubes and laryngeal masks.

BACKGROUND ART

Nasogastric tubes and related devices are described in U.S. Pat. Nos. 5,643,230, 5,417,664, 5,011,474, 5,000,175, 4,821,715, 4,787,894, 4,735,607, 4,699,138, 4,508,533, and 4,214,593. Nasogastric tubes and related devices are also described in the following patents and published patent applications: EP 0500778, JP 10179677, WO 9716154, WO 9631248, and WO 8000538.

Nasogastric tubes are used to aspirate food contents from the stomach or to feed patients who are unable to safely feed themselves. Nasogastric tubes are commonly used in the operating room, intensive care units, home care, and in hospice settings. Prior art nasogastric tubes are frequently used to aspirate stomach contents. However, in some cases, aspiration of the stomach contents results in micro-aspirations that can cause nosocomial infections.

Similar problems can occur with prior art laryngeal masks. Laryngeal masks are used to provide ventilation and are commonly used in the operating room and in situations where it is difficult to insert an endotracheal tube. Prior art laryngeal masks and related devices are described in U.S. Pat. Nos. 4,351,328, 4,509,514, 4,995,388, 5,241,956, 5,303,697, 5,355,879, 5,632,271, 5,878,745, 6,631,720 and 6,895,966 and in published international patent application no. WO 1994/02191. A disadvantage of prior art laryngeal masks is that there is no protection from aspiration into the lungs of gastric contents or saliva regurgitated into the hypopharynx and pharynx.

DISCLOSURE OF THE INVENTION

The present invention is directed to, in one aspect, a medical apparatus comprising a nasogastric tube with hypopharyngeal suctioning capability. An important feature of the medical apparatus of the present invention is that it includes a suction intake in the area of the hypopharynx which effects capturing microaspirations as well as larger regurgitated material that reaches the hypopharynx. A significant advantage of the present invention is that it reduces infection rates in intubated patients. In accordance with one embodiment of the invention, the medical apparatus comprises a flexible nasogastric tube for insertion through a patient's nose. The nasogastric tube has a first end and a distal, second end that defines an opening. The nasogastric tube has a length sufficient to allow the opening to be positioned in a patient's stomach. The medical apparatus further comprises a flexible oropharyngeal tube for insertion through a patient's mouth. The oropharyngeal tube has a first end and a distal, second end that defines a suction intake. The oropharyngeal tube has a length that is less than the length of the nasogastric tube and which allows the suction intake to be positioned in a patient's hypopharynx region. The medical apparatus further comprises a section of tube joined to and in communication with the flexible nasogastric and oropharyngeal tubes. The section of tube is configured to be joined to a suction apparatus that creates suction within the oropharyngeal tubes. This suction causes microaspirations and regurgitated material in the hypopharynx region to be sucked into the suction intake of the oropharyngeal tube.

In another aspect, the present invention is related to a medical apparatus comprising a laryngeal mask and a suction tube attached to the laryngeal mask. The suction tube includes a plurality of suction intakes that suck oropharyngeal secretions from the patient's mouth and the back of the patient's throat. Thus, in one embodiment, this medical apparatus comprises a laryngeal mask having a front side and rear side wherein the rear side faces the back of a patient's throat when the laryngeal mask is used in a patient, and a flexible suction tube attached to and extending along the rear side of the laryngeal mask. The suction tube comprises a plurality of suction intakes for suctioning oropharyngeal secretions from the patient's mouth and back of the patient's throat and has an opening that is configured to be connected to an apparatus for producing suction within the flexible suction tube.

In a further aspect, the present invention is directed to a laryngeal mask apparatus (1000) for facilitating ventilation of a patient, comprising a mask (1001) comprising a front side (1002) and a rear side (1004) that faces the back of a patient's throat when the mask (1001) is positioned within a patient's throat, and a flexible breathing tube (1010) that has an interior (1011) for the flow of air. The flexible breathing tube (1010) is in communication with the mask (1001). A joint section (1006) is attached to the rear side (1004) of the mask portion (1001). The flexible breathing tube (1010) is connected to the joint section (1006) so that air in flexible breathing tube (1010) can flow through the joint section (1006) and into the mask (1001). The flexible breathing tube (1010) is configured for use with a ventilating system. The laryngeal mask apparatus (1000) further comprises an additional flexible tube (1018) comprising an interior (1019), a first portion (1018A) and a second portion (1018B) that is configured to be connected to a device that facilitates creation of suction within interior (1019). A substantial portion of first portion (1018A) is joined or attached to the exterior surface of joint section (1006). The additional flexible tube (1018) extends to a distal end (1018C) which is part of the first portion (1018A). The first portion (1018A) has a plurality of suction ports (1009) in communication with the interior (1019). The suction ports (1009) are located on the first portion (1018A) such that the suction ports (1009) face the back of the patient's throat when the mask (1001) is positioned within a patient's throat so that the suction ports (1009) suck in fluids and secretions in a patient's hypopharyngeal region when suction is created within interior (1019). The additional flexible tube (1018) further comprises an air entry hole (1050) in the second portion (1018B) and an air exit hole (1060) in the first portion (1018A). The section of first portion (1018A) having distal end (1018C) and air exit hole (1060) is not joined or attached to joint section (1006) or rear side (1004) of mask (1001), but instead is spaced apart from mask (1001) such that air exit hole (1060) is not blocked by mask (1001). The additional flexible tube (1018) further comprises a flexible air capillary tube (1020) that is located within the interior (1019) of additional flexible tube (1018). The flexible air capillary tube (1020) includes a first open end (1020A) that is in communication with the air entry hole (1050) and a second open end (1020B) that is in communication with the air exit hole (1060). When suction is created within interior (1019), air is drawn into air entry hole (1050) and enters first open end (1020A) of air capillary tube (1020) wherein the air then flows through air capillary tube (1020), exits second open end (1020B) and then exits air exit hole (1060), whereby when the mask (1001) is positioned within a patient's throat and suction is created within interior (1019), the air exiting air exit hole (1060) decreases the direct suction forces on the mucosa of the patient's throat.

In one embodiment, the aforementioned substantial portion of first portion (1018A) is also joined or attached to the rear side (1004) of mask (1001).

The additional tube (1018) has a middle portion that is between first portion (1018A) and the second portion (1018B). The middle portion is joined or attached to the flexible breathing tube (1010).

The laryngeal mask apparatus (1000) further comprises a suction tube connector (1024) that is connected to the second portion (1018B) of additional flexible tube (1018). The suction tube connector (1024) further comprises a suction enablement device (1025) to enable creation of suction within interior (1019).

Mask (1001) further comprises an inflatable tubular ring (1005). The laryngeal mask apparatus (1000) further comprises an air tube (1012) that is connected to the inflatable tubular ring (1005) and, when connected to an air source, provides an air stream that inflates inflatable tubular ring (1005). The laryngeal mask apparatus (1000) further comprises a connector (1026) that has a first portion (1028) that is inserted into the flexible breathing tube (1010) and a second portion (1030) that is configured for connection to a ventilating system that provides air or oxygen or anesthesia.

In a further aspect, the present invention is directed to a laryngeal mask apparatus (1000) for facilitating ventilation of a patient, comprising a mask (1001) that comprises a front side (1002) and a rear side (1004) that faces the back of a patient's throat when the mask (1001) is positioned within a patient's throat. The laryngeal mask apparatus (1000) further comprises a flexible breathing tube (1010) having an interior (1011) for the flow of air, and a joint section (1006) that is joined or attached to the rear side (1004) of the mask (1001). The flexible breathing tube (1010) is connected the joint section (1006) so that air in the flexible breathing tube (1010) flows through the joint section (1006) and into the mask (1001). The flexible breathing tube (1010) is configured for use with a ventilating system. The laryngeal mask apparatus (1000) further comprises an additional flexible tube (1018) that comprises an interior (1019), a first portion (1018A) and a second portion (1018B) that is configured to be connected to a device that facilitates creation of suction within interior (1019). A substantial portion of first portion (1018A) is joined or attached to the exterior surface of joint section (1006). The additional flexible tube (1018) extends to a distal end (1018C) which is part of the first portion (1018A). The first portion (1018A) has a plurality of suction ports (1009) in communication with the interior (1019). The suction ports (1009) are located on the first portion (1018A) at particular positions such that the suction ports (1009) face the back of the patient's throat when the mask (1001) is positioned within a patient's throat so that the suction ports (1009) suck in fluids and secretions in a patient's hypopharyngeal region when suction is created within interior (1019). The additional flexible tube (1018) further comprises an air entry hole (1050) in the second portion (1018B) and an air exit hole (1060) in the first portion (1018A). The additional flexible tube (1018) further comprises a flexible air capillary tube (1020) that is located within the interior (1019) of additional flexible tube (1018). The flexible air capillary tube (1020) includes a first open end (1020A) that is located so that it is near the air entry hole (1050) and a second open end (1020B) that is located so that it is near the air exit hole (1060). When suction is created within interior (1019), air is drawn into air entry hole (1050) and enters first open end (1020A) of air capillary tube (1020) wherein the air then flows through air capillary tube (1020), exits second open end (1020B) and then exits air exit hole (1060), whereby when the mask (1001) is positioned within a patient's throat and suction is created within interior (1019), the air exiting air exit hole (1060) decreases the direct suction forces on the mucosa of the patient's throat. In one embodiment, the aforementioned substantial portion of first portion (1018A) is also joined or attached to rear side (1004) of mask (1001). In one embodiment, the additional flexible tube (1018) has a middle portion that is between first portion (1018A) and the second portion (1018B). The middle portion is joined or attached to the flexible breathing tube (1010).

BRIEF DESCRIPTION OF THE DRAWINGS

The features of the invention are believed to be novel. The figures are for illustration purposes only and are not drawn to scale. The invention itself may best be understood by reference to the detailed description which follows taken in conjunction with the accompanying drawings in which.

DETAILED BEST MODE FOR CARRYING OUT THE INVENTION

Figure 1:
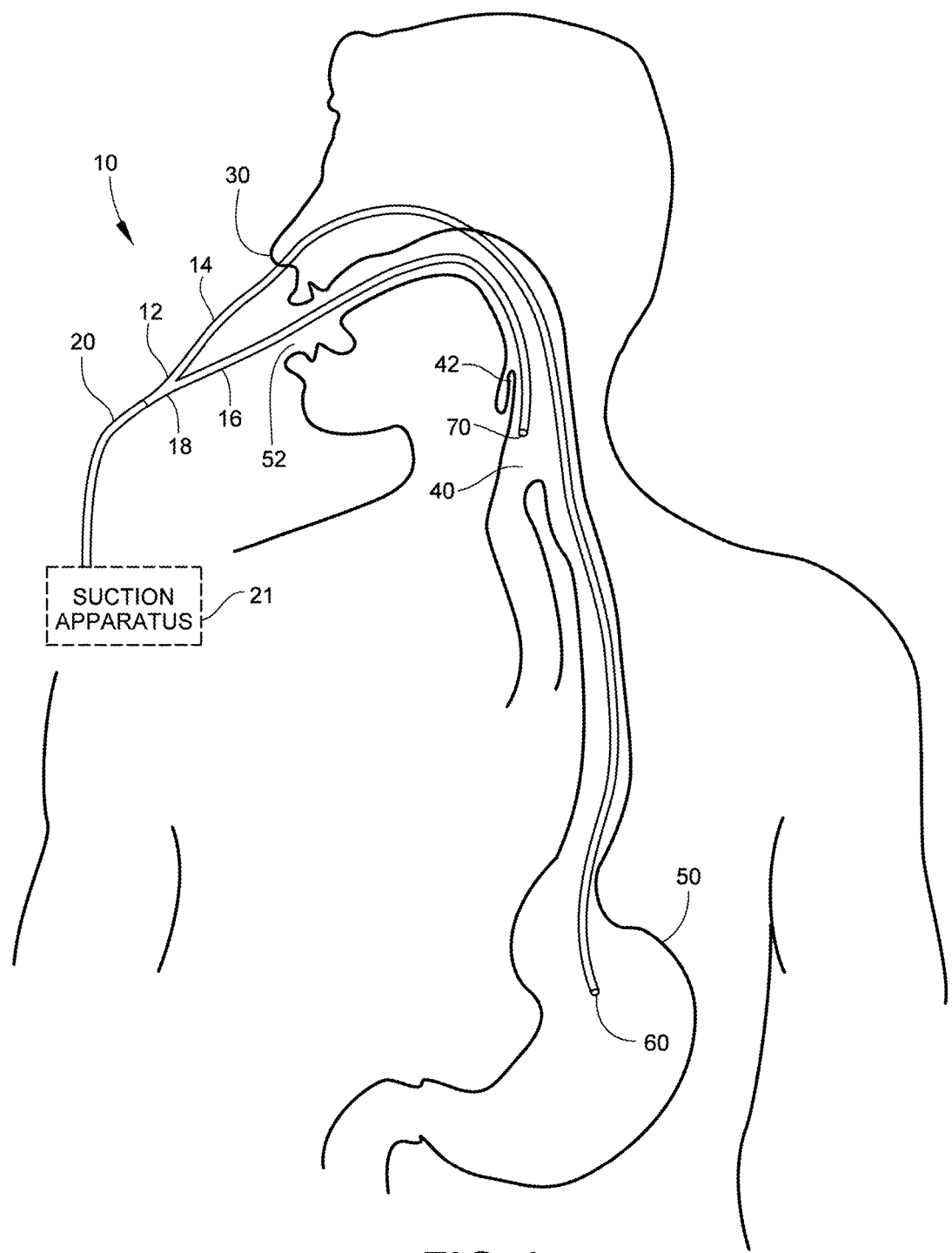
FIG. 1 is a diagrammatic view, generally in side elevation, of a medical apparatus in accordance with one embodiment of the invention, the same being shown used in a patient.

Referring to FIG. 1, there is shown a diagrammatic view of one embodiment of the medical apparatus of the present invention. This medical apparatus, generally indicated by reference numeral 10, comprises tube structure 12. Tube structure 12 comprises nasogastric tube section 14 and oropharyngeal tube section 16. The interior of nasogastric tube section 14 is known as the lumen. Similarly, the interior of oropharyngeal tube section 16 is known as the lumen. Nasogastric tube section 14 and oropharyngeal tube section 16 are joined together at tube section 18 so as to form a generally "Y" shaped configuration. Tube section 18 is configured to be connected to tube section 20. Tube section 20 is configured to be connected to an external apparatus 21 (shown in phantom). For example, such external apparatus 21 can be a suction apparatus for creating suction within tube structure 12. In another example, the aforesaid external apparatus can be a food source for feeding a patient that is unable to feed himself or herself.

As shown in FIG. 1, nasogastric tube section 14 has a sufficient length that allows it to be inserted through the patient's nose 30, through the hypopharnyx region 40 (which is just below epiglottis 42) and into the patient's stomach 50. Nasogastric tube section 14 has opening 60 that is located in the patient's stomach 50. When tube section 20 is connected to suction apparatus 21, the opening 60 functions as a suction intake that effects aspiration of food contents from the stomach. As a result of the suction, the aspirated food contents travel through nasogastric tube section 14 and into a container (not shown) in suction apparatus 21. On the other hand, if tube section 20 is connected to a food source, then opening 60 functions as an output for this food.

As shown in FIG. 1, oropharyngeal tube section 16 is inserted through the patient's mouth 52 and has a length that is relatively shorter than the length of nasogastric tube section 14. Oropharyngeal tube section 16 has suction intake 70. The length of oropharyngeal tube section 16 is such that suction intake 70 is positioned in hypopharynx region 40. When tube section 20 is connected to suction apparatus 21, suction intake 70 of oropharyngeal tube section 16 sucks in microaspirations and regurgitated material located in hypopharynx region 40 thereby removing such microaspirations and regurgitated material from hypopharynx region 40. Such microaspirations and regurgitated material travel through oropharyngeal tube section 16 and into the aforesaid container (not shown) in suction apparatus 21. Thus, suction intake 70 substantially reduces the risk of infection due to aspirations from the stomach 50 moving into the mouth 52.

In one embodiment, nasogastric tube section 14 and oropharyngeal tube section 16 are fabricated from commercially available flexible, soft plastic material, similar to the material used to fabricate conventional endotracheal tubes. In one embodiment, preferably, the internal diameter of such commercial plastic tubing is between about 5 mm and 10 mm.

Figure 2:
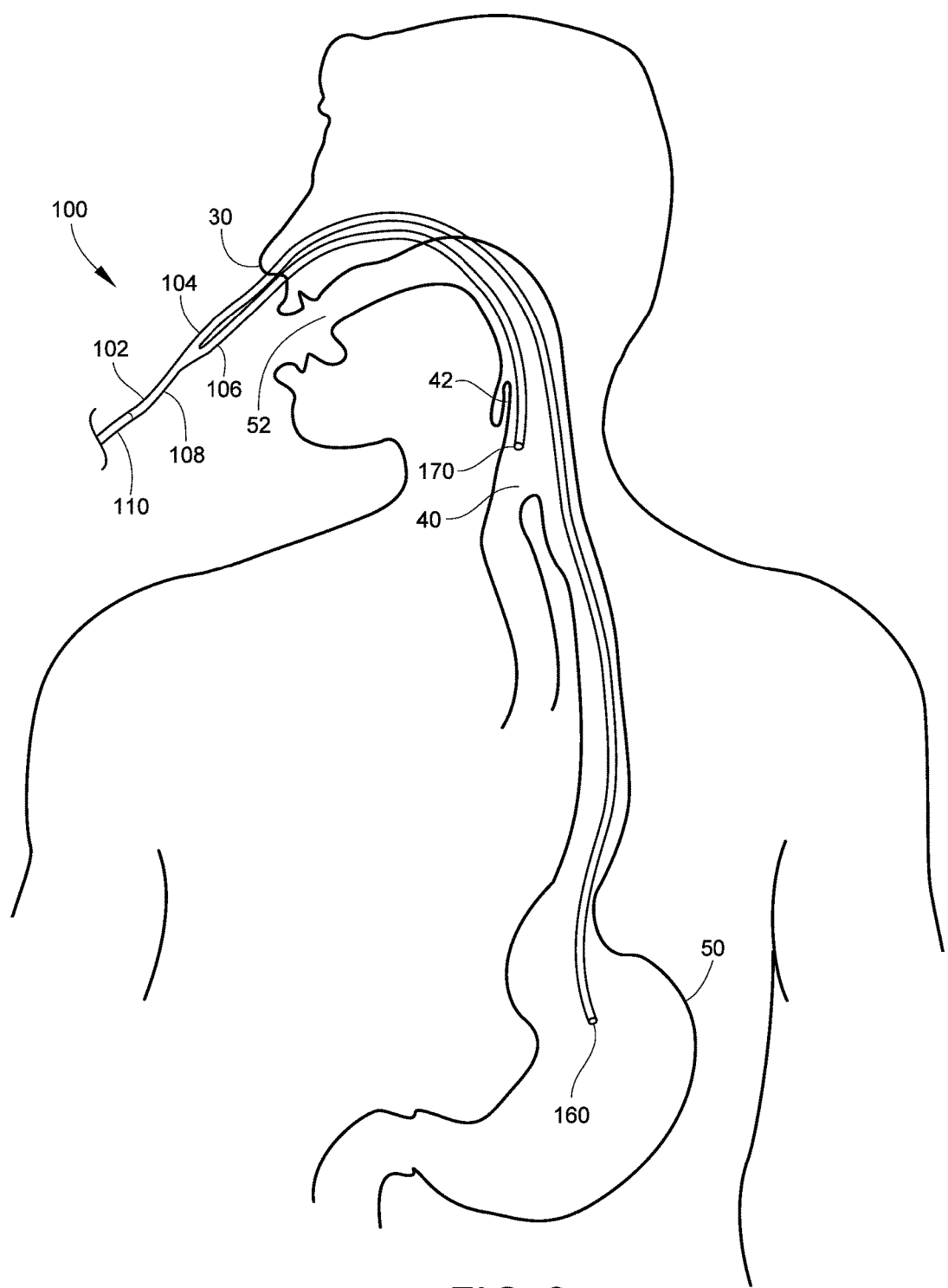
FIG. 2 is a diagrammatic view, generally in side elevation, of a medical apparatus in accordance with another embodiment of the invention, the same being shown used in a patient.

Referring to FIG. 2, there is shown medical apparatus 100 in accordance with another embodiment of the present invention. Medical apparatus 100 comprises tube structure 102. Tube structure 102 comprises nasogastric tube section 104, nasopharyngeal tube section 106, and tube section 108. Nasogastric tube section 104 and nasopharyngeal tube section 106 are joined together at tube section 108 so as to form a generally "Y" shaped configuration. Both nasogastric tube section 104 and nasopharyngeal tube section 106 are inserted through the patient's nose 30. Tube section 108 is configured to be connected to tube section 110. Tube section 110 is configured to be connected to an external apparatus (not shown). For example, such an external apparatus can be a suction apparatus such as suction apparatus 21 described in the foregoing description. Such a suction apparatus produces suction within tube structure 102. Thus, tube section 108 and tube section 110 have the same structure and perform the same functions as tube section 18 and tube section 20, respectively, of medical apparatus 10 described in the foregoing description. Nasogastric tube section 104 has opening 160. Nasogastric tube section 104 has a length that ensures that opening 160 is positioned in the patient's stomach 50. Nasogastric tube section 104 performs the same function as nasogastric tube section 14 (see FIG. 1). Nasopharyngeal tube section 106 has suction intake 170. Nasopharyngeal tube section 106 has a predetermined length that is less than the length of nasogastric tube section 104. This predetermined length of nasopharyngeal tube section 106 allows suction intake 170 to be positioned in the patient's hypopharynx region 40. Suction intake 170 performs the same function as suction intake 70 of oropharyngeal tube section 16 shown in FIG. 1. When the aforementioned suction apparatus is connected to tube section 110, suction intake 170 sucks in microaspirations and regurgitated material located in hypopharynx region 40 thereby removing such microaspirations and regurgitated material in hypopharynx region 40. Thus, suction intake 170 substantially reduces the risk of infection due to aspirations from stomach 50 moving into mouth 52.

Figure 3A:
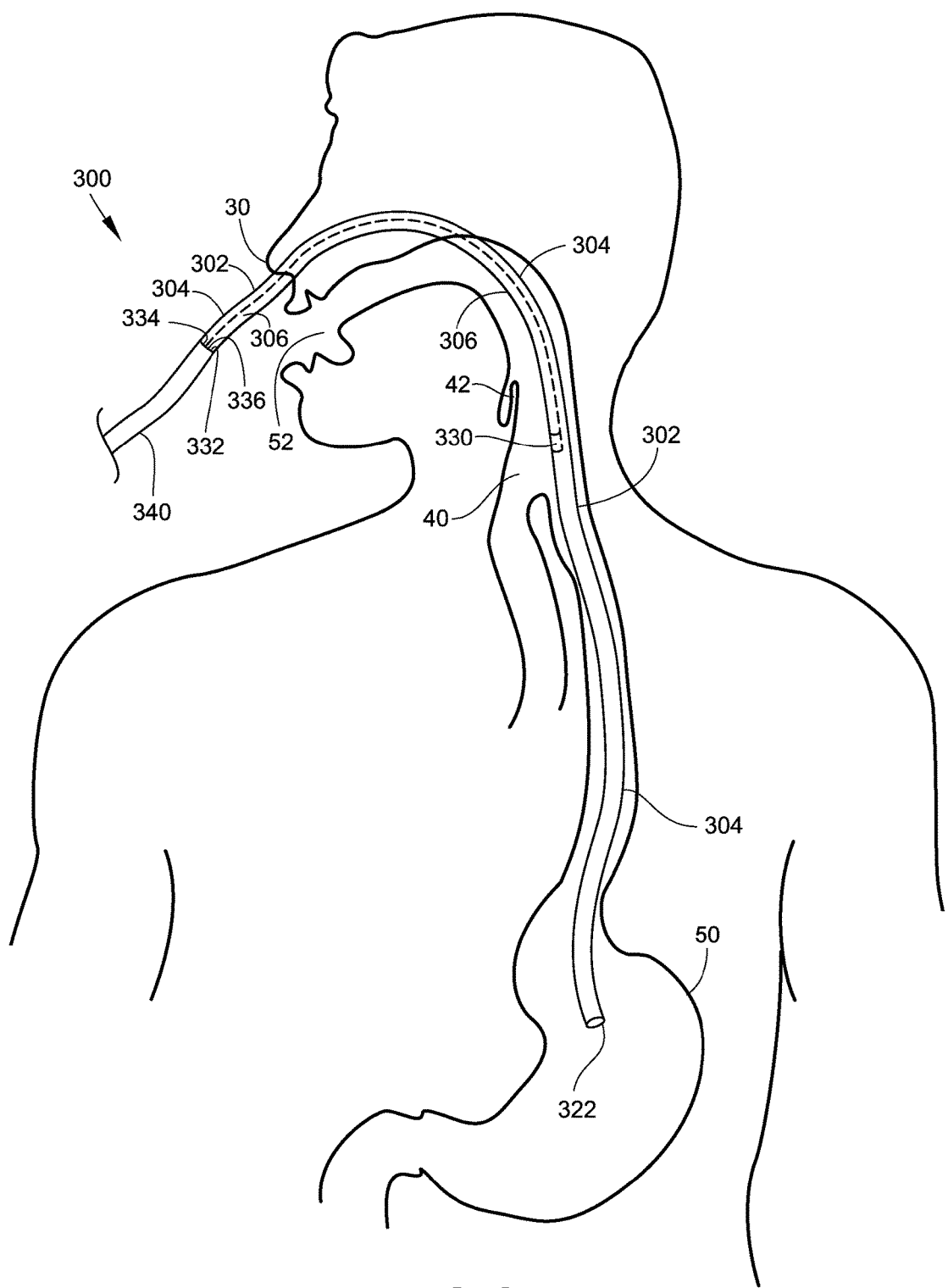
FIG. 3A is a diagrammatic view, generally in side elevation, of a medical apparatus in accordance with another embodiment of the invention, the same being shown used in a patient.
Figure 3B:
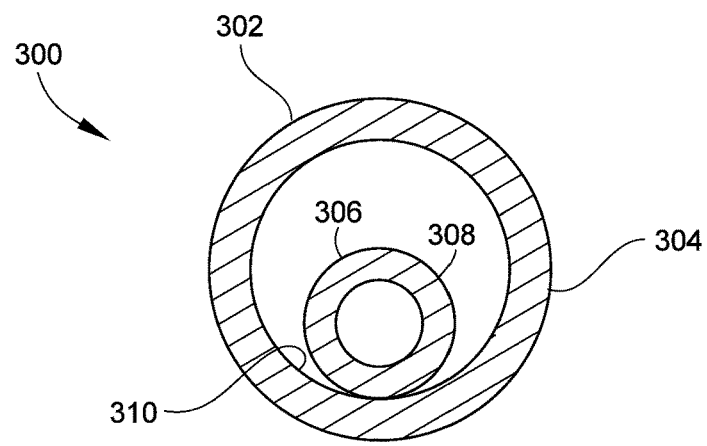
FIG. 3B is a cross-sectional view of the tube structure shown in FIG. 3A.
Figure 3C:
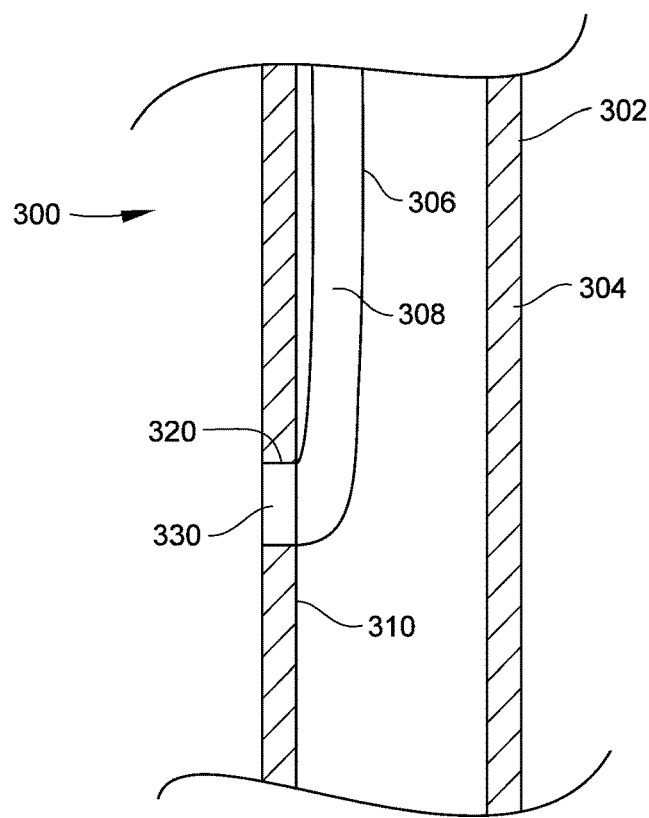
FIG. 3C is an enlarged view of a portion of the view of FIG. 3A.
Figure 3D:
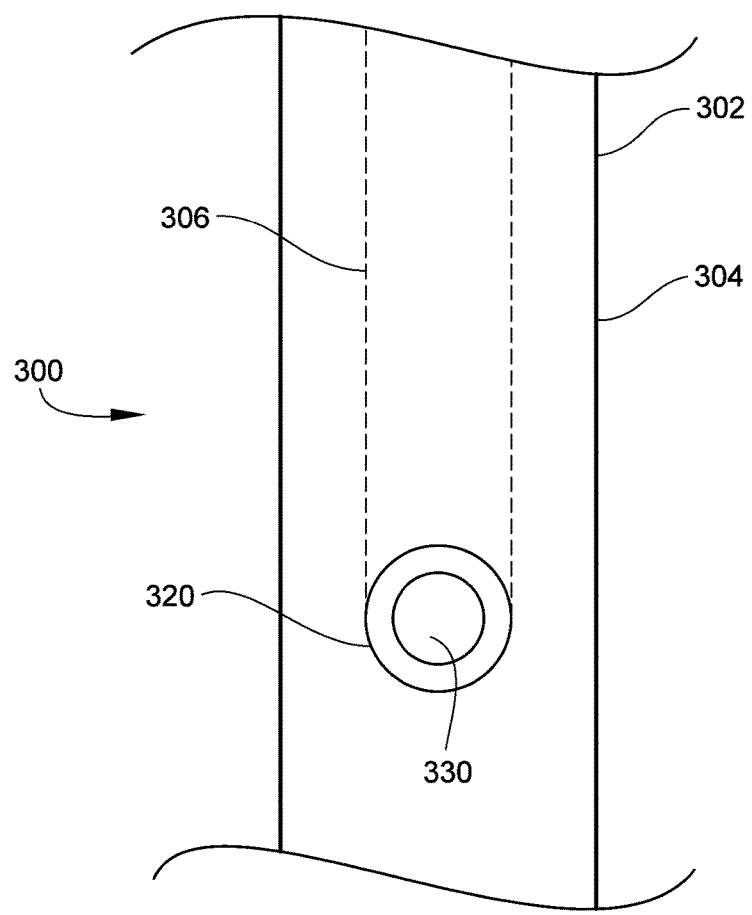
FIG. 3D is an elevational view of a portion of the tube structure shown in FIG. 3A.
Figure 4:
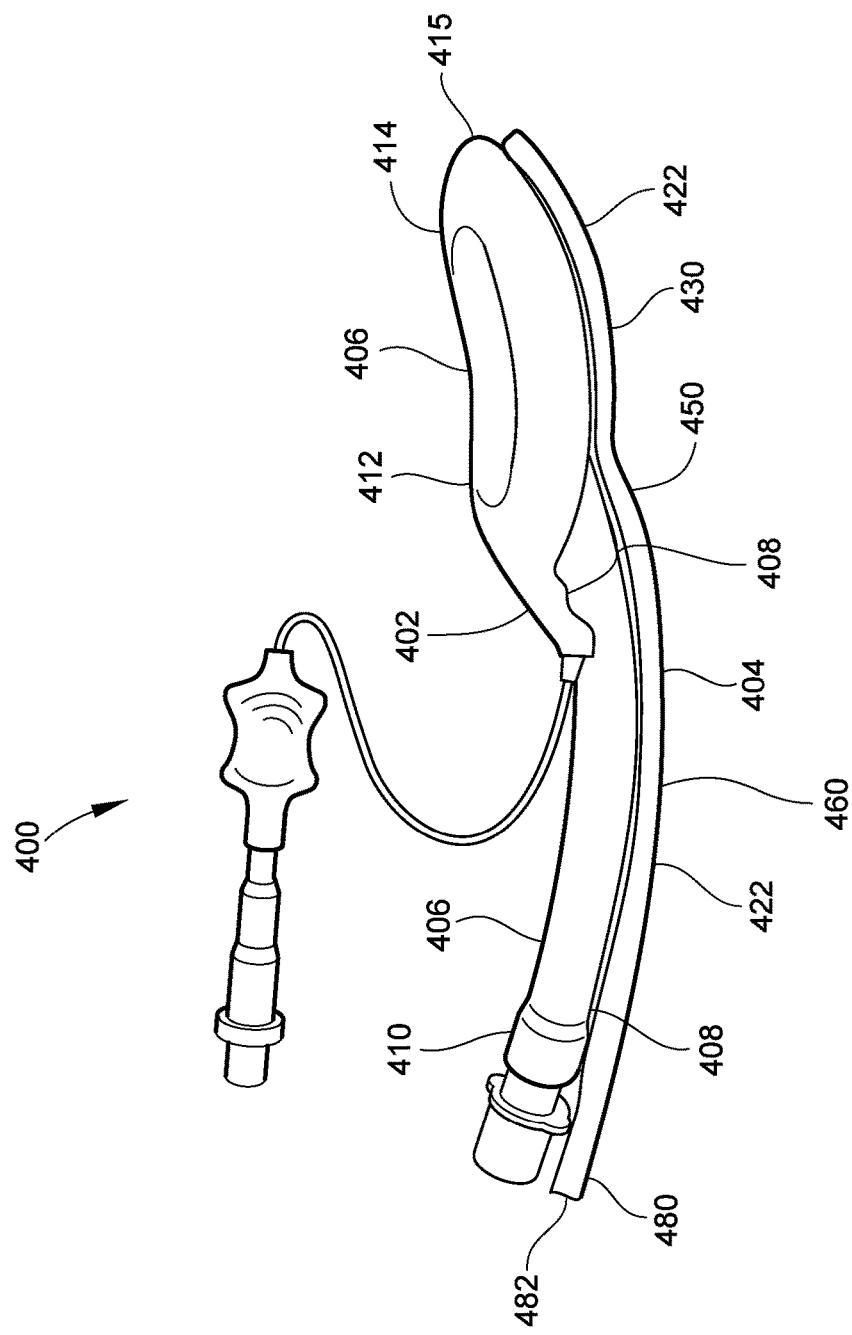
FIG. 4 is a perspective view of a medical apparatus in accordance with another embodiment of the invention.
Figure 5:
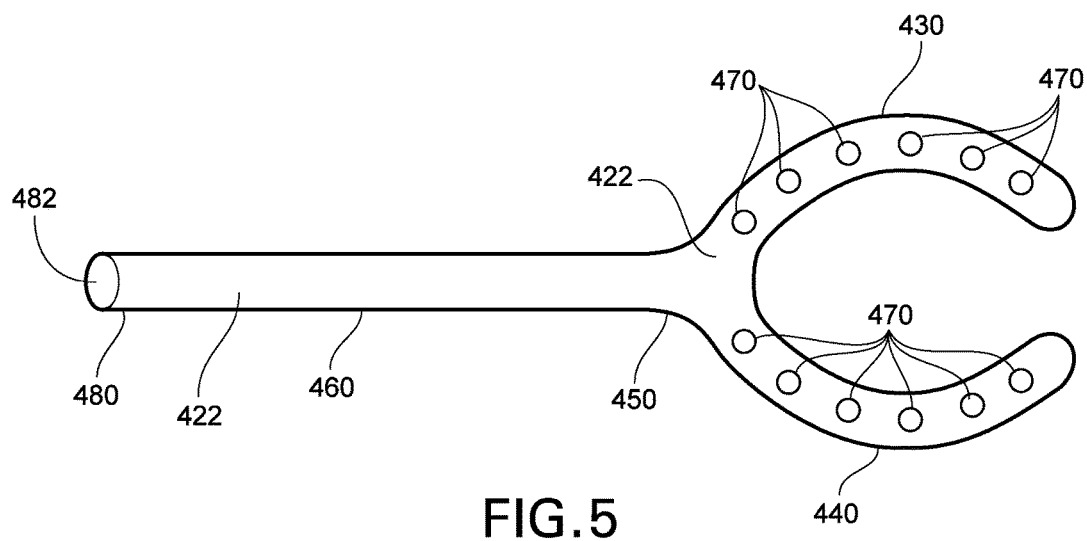
FIG. 5 is a plan view of the front side of a suction tube depicted in FIG. 4.
Figure 6:
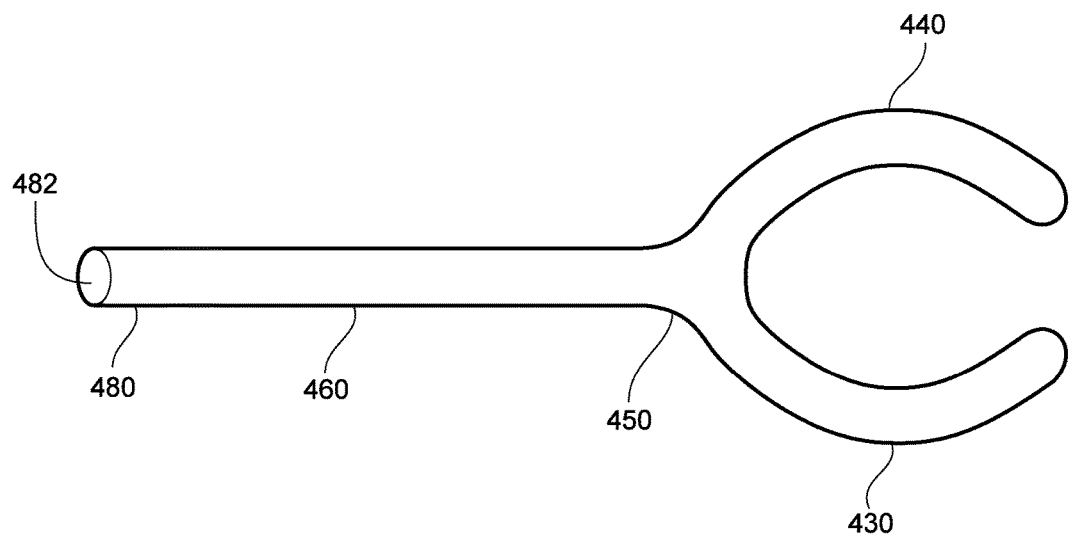
FIG. 6 is a plan view of the rear side of the suction tube shown in FIG. 5.

Referring to FIGS. 3A-D, there is shown medical apparatus 300 in accordance with a further embodiment of the present invention. Medical apparatus 300 comprises tube structure 302 which is configured to be inserted through the patient's nose 30. Tube structure 302 comprises an outer tube 304 and an inner conduit 306. Thus, inner conduit 306 is positioned within outer tube 304. In one embodiment, as shown in FIG. 3B, inner conduit 306 is a tube having an outer surface 308. In such an embodiment, outer surface 308 is attached to inner surface 310 of outer tube 304. In another embodiment, inner conduit 306 is integrally formed with outer tube 304 during the manufacture of tube structure 302. Outer tube 304 includes openings 320 and 322. The length of outer tube 304 is such that opening 322 is located in the patient's stomach 50. Opening 322 serves the same purpose as opening 60 (see FIG. 1) and opening 160 (see FIG. 2). As shown in FIGS. 3A and 3C, the length of inner conduit 306 is less than the length of outer tube 304. Tube structure 302 has a predetermined length that allows opening 320 to be located in the patient's hypopharynx region 40. Inner conduit 306 includes opening 330 that is aligned and in communication with opening 320 in outer tube 304. Opening 330 functions as a suction intake port or opening.

Referring to FIG. 3A, tube structure 302 has end 332. Outer tube 304 has opening 334 that is adjacent to end 332. Inner conduit 306 has opening 336 that is adjacent to end 332. Medical apparatus 300 includes tube section 340 that is joined to end 332 of tube structure 302. Tube section 340 serves the same purpose as tube section 20 (see FIG. 1) and is configured to be connected to an external apparatus such as suction apparatus 21 described in the foregoing description. When a suction apparatus is connected to tube section 340, suction is produced within tube structure 302 which results in microaspirations and regurgitated material located in hypopharynx region 40 to be sucked into opening 330. Thus, microaspirations and regurgitated material in hypopharynx region 40 are removed thereby substantially reducing the risk of infection due to aspirations from stomach 50 moving into mouth 52.

The medical apparatus shown in FIGS. 1-3D provides many important advantages. One such advantage is that the suction intake in hypopharynx region 40 captures microaspirations as well as relatively larger regurgitated material and particles that enter the hypopharynx. This feature reduces the risk of infection due to aspirations from the stomach moving into the mouth. This medical apparatus can be used during surgery for patients with any of the following conditions:
a) gastric obstruction;
b) gastroesophageal reflux disease (GERD);
c) diabetes patients who have full stomachs;
d) pregnancy (enlarged abdomens and at risk for aspiration);
e) cancer patients (poor digestion, enlarged abdominal tumors, and/or vomiting); and.
f) patients on medications that increase incidence of nausea and vomiting.

This medical apparatus also can be used in the ICU (Intensive Care Unit) for (i) intubated patients who have increased risk of microaspiration in the presence of a nasogastric tube and an endotracheal tube, such as patients with bowel obstruction, (ii) patients with total parental nutrition who are not intubated but require a nasogastric tube to prevent aspiration, and (iii) patients who have gastroparesis, cancer, diabetes, pregnancy and other conditions where patients have a full stomach and require a nasogastric tube.

In accordance with another embodiment of the invention, medical apparatus 400, shown in FIGS. 4-7, is an improved laryngeal mask configured to effect suctioning the hypopharynx region. Medical apparatus 400 comprises laryngeal mask 402 and suction tube 404. In a preferred embodiment, laryngeal mask 402 is configured as the laryngeal mask described in U.S. Pat. No. 4,509,514, the disclosure of which patent is hereby incorporated by reference. Laryngeal mask 402 has a front side 406 and rear side 408. Suction tube 404 is located at the rear side 408 of laryngeal mask 402. In one embodiment, suction tube 404 is integrally formed with laryngeal mask 402 during the manufacture of medical apparatus 400. In another embodiment, suction tube 404 is a separate component that is attached to the rear side 408 of laryngeal mask 400. In such an embodiment, any suitable technique can be used to attach suction tube 404 to rear side 408 of laryngeal mask 400. Laryngeal mask 402 comprises flexible breathing tube 410 and mask portion 412 with an inflatable tubular ring 414. Inflatable tubular ring 414 has distal end 415. Suction tube 404 is preferably fabricated from soft plastics material, similar to that conventionally used for endotrachael tubes. Suction tube 404 comprises a rear side that is attached to rear side 408 of laryngeal mask 402. Suction tube 404 includes front side 422. Suction tube 404 further includes tube sections 430 and 440 that are joined together at middle tube section 450. Sections 430 and 440 are attached to the rear side of mask portion 412. Suction tube 404 further includes tube section 460 that is connected to middle tube section 450 and extends along the rear side of flexible breathing tube 410. Each tube section 430 and 440 has a plurality of suction ports 470 formed on front side 422. Suction tube 404 has end portion 480 that defines opening 482. End portion 480 is configured to be connected to a suction hose (not shown) that is connected to an external suction apparatus (not shown) such as suction apparatus 21 described in the foregoing description.

Figure 7:
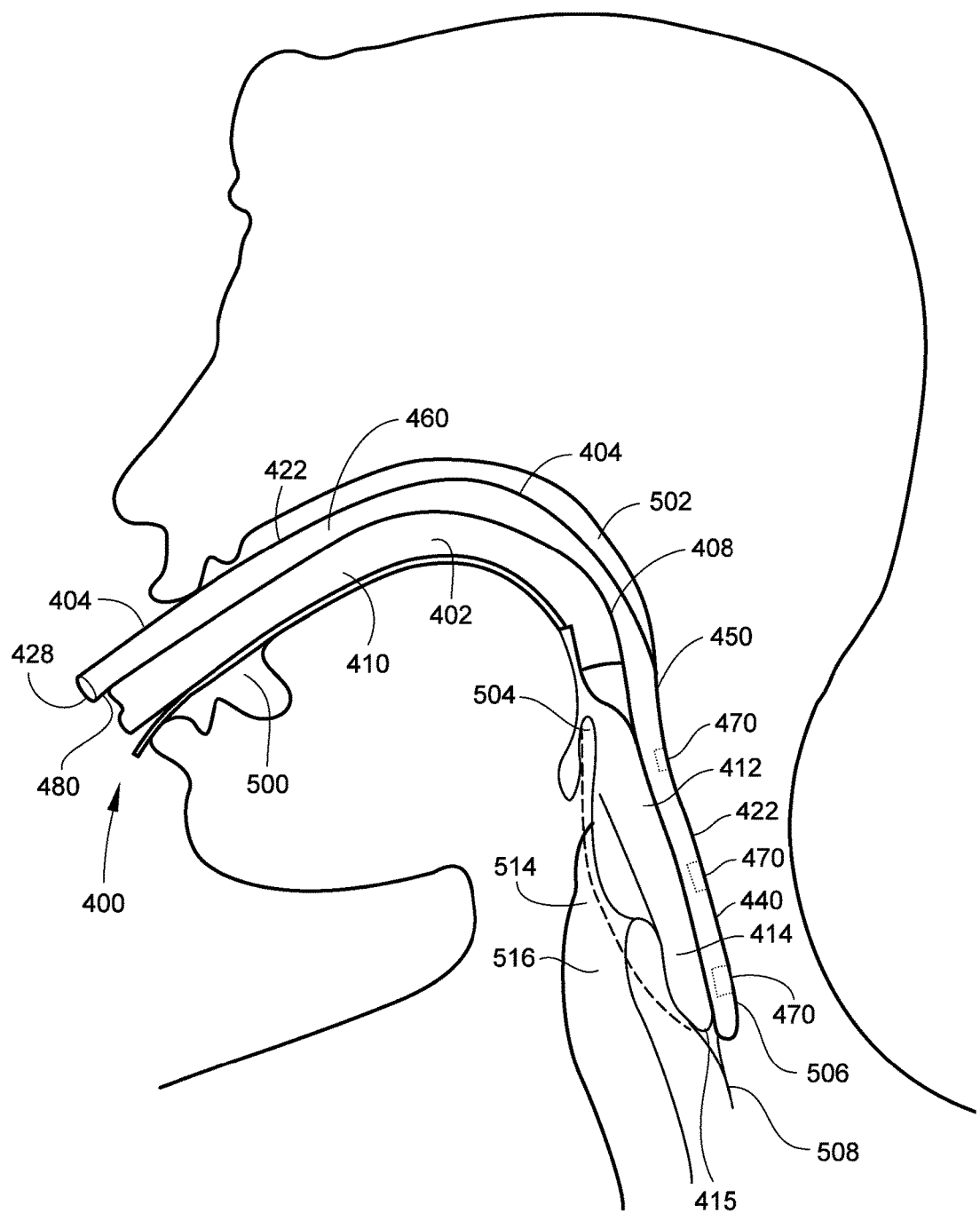
FIG. 7 is a diagrammatic view of the medical apparatus of FIG. 4 used in a patient.

Referring to FIG. 7, when in use, medical apparatus 400 is inserted into the patient's mouth 500 and down through the patient's throat 502 past the epiglottis 504 until mask portion 412 comes to rest with distal end 415 of inflatable ring 414 in the base 506 of throat 502, lying against the upper end of the normally closed esophagus 508. Suction ports 470 face the back of throat 502. Inflatable ring 414 is then inflated as shown to seal around inlet 514 to larynx 516. The patient's airway is thus secure and unobstructed and flexible tube 410 is then connected directly to the conventional anesthetic circuit hosing for either positive pressure or spontaneous breathing. End portion 480 of suction tube 404 is then connected to a suction apparatus to allow suction ports 470 to suck oropharyngeal secretions from the mouth and the back of the throat 502. Such secretions are made not only from the patient's stomach, but also from the salivary glands in the mouth.

Medical apparatus 400 provides a laryngeal mask with increased versatility which can be used in many situations including patients with gastroesophageal reflux disease, gastric obstruction, diabetes with full stomachs and cancer (e.g. poor digestion, enlarged abdomen, nausea and vomiting). The laryngeal mask of the present invention can be used by patients during pregnancy (e.g. enlarged abdomen and at risk of aspiration).

Figure 8:
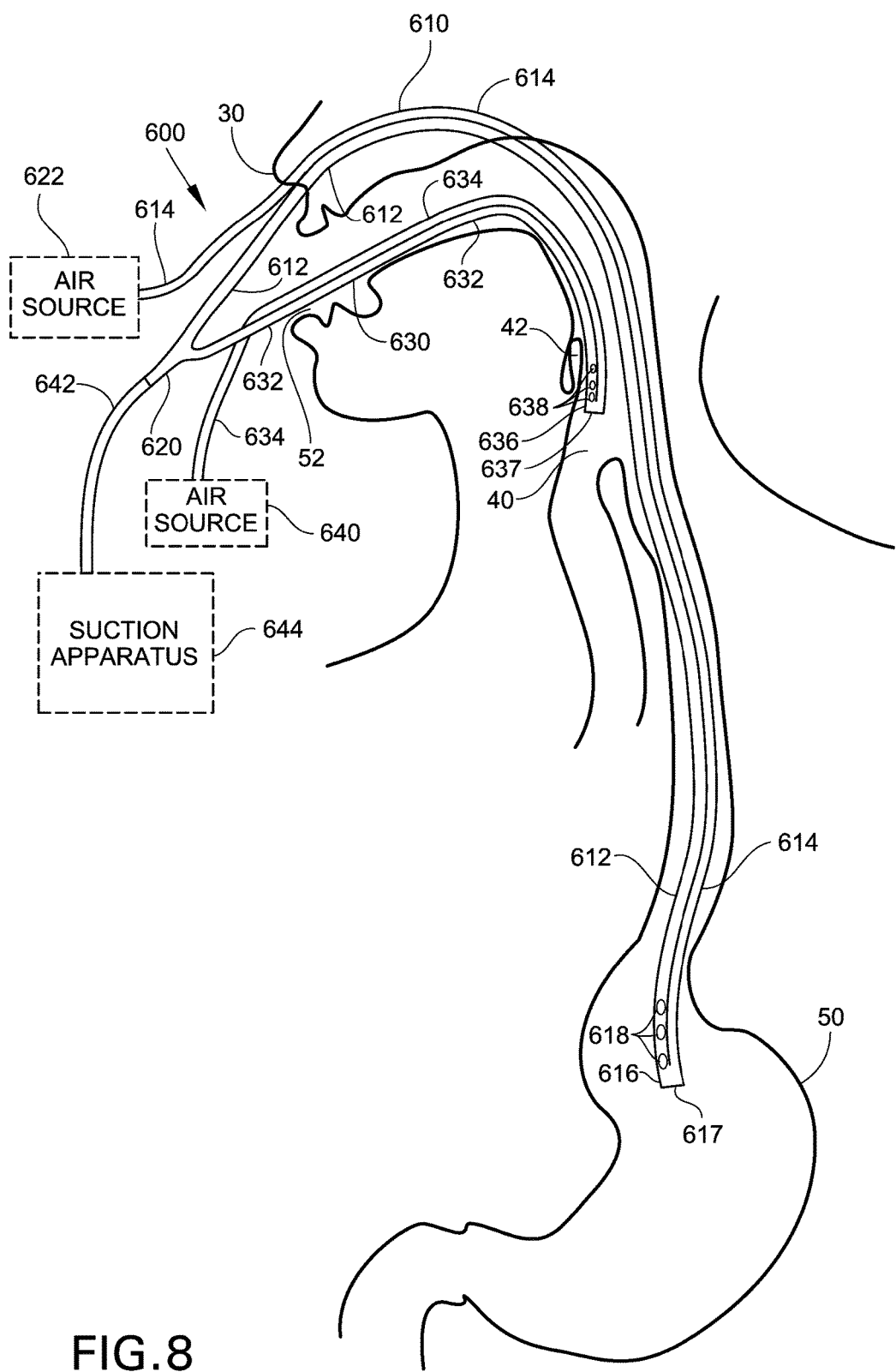
FIG. 8 is a diagrammatic view, generally in side elevation, of a medical apparatus in accordance with a further embodiment of the invention, the same being shown used in a patient.
Figure 10:
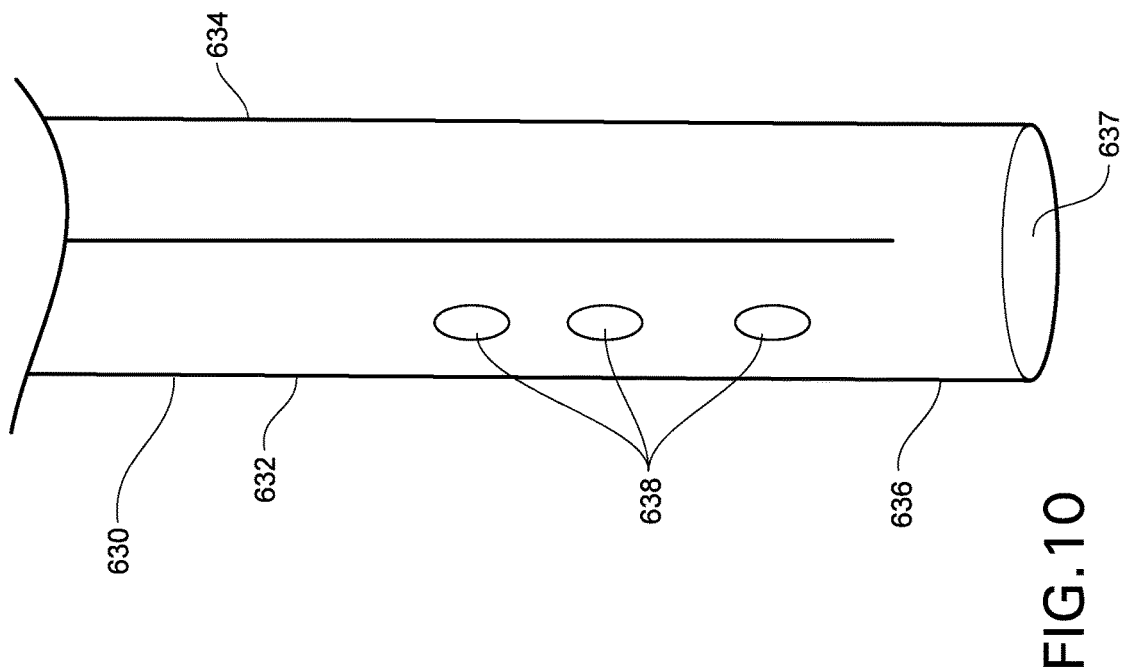
FIG. 10 is an enlarged view of a portion of the view shown in FIG. 8.
Figure 9:
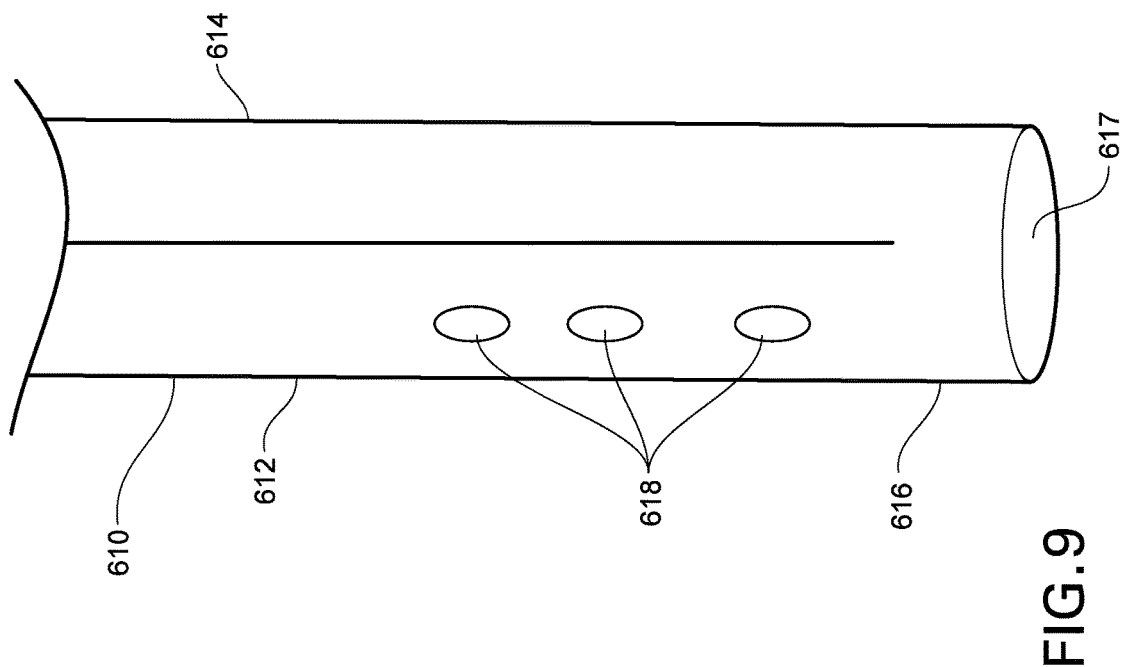
FIG. 9 is an enlarged view of a portion of the view shown in FIG. 8.

Referring to FIGS. 8, 9 and 10, there is shown medical apparatus 600 in accordance with another embodiment of the invention. Medical apparatus 600 is configured for the situation wherein continuous suction is necessary. As will be shown by the ensuing discussion, medical apparatus 600 prevents collapse of the hypopharynx and stomach walls while continuous suctioning is occurring and also prevents damage to stomach and hypopharynx tissues. Medical apparatus 600 generally comprises nasogastric tube structure 610. Nasogastric tube structure 610 comprises suction tube 612 and air tube 614. Suction tube 612 and air tube 614 are joined together at end portion 616. End portion 616 defines opening 617. Opening 617 is in communication with suction tube 612 and air tube 614. In one embodiment, the portions of suction tube 612 and air tube 614 that extend from end portion 616 are attached together until they exit the patient's body. The length of nasogastric tube structure 610 is such that end portion 616 is positioned in stomach 50. Suction tube 612 has suction intakes 618. Suction tube 612 and air tube 614 separate outside of the patient's body in order to allow these two tubes to be connected to separate medical equipment. Suction tube 612 is joined to tube section 620 and air tube 614 is joined to air source 622.

Medical apparatus 600 further comprises oropharyngeal tube structure 630. Oropharyngeal tube structure 630 includes suction tube 632 and air tube 634 which are joined at end portion 636. End portion 636 defines opening 637. Oropharyngeal tube structure 630 includes suction intakes 638. Oropharyngeal tube structure 630 has a predetermined length that is shorter than the length of tube structure 610 thereby allowing end portion 636 to be positioned in hypopharynx region 40. The portions of suction tube 632 and air tube 634 that extend from end portion 636 are attached together until these tubes exit the patient's body. Suction tube 632 is joined to tube section 620. Air tube 634 is connected to air source 640. Tube section 620 is joined to intermediate tube section 642. Intermediate tube section 642 is connected to a suction apparatus 644. Air source 622 provides air to air tube 614. This air exits air tube 614 at opening 617. Air source 640 provides air to air tube 634. Such air exits air tube 634 at opening 637 in tube structure 630. Suction apparatus 644 produces suction within suction tubes 612 and 632. As a result of such suction, stomach contents are sucked into suction intakes 618 and microaspirations and regurgitated material and particles in hypopharynx region 40 are sucked through section intakes 638. The air in air tube 614 prevents collapse of the stomach 50 and prevents suction intakes 618 from contacting and sucking the stomach walls. Thus, damage to the tissues of the stomach wall and mucosa is prevented. Similarly, the air in air tube 634 enters hypopharynx region 40 and prevents a collapse of the hypopharynx. This air also prevents suction intakes 638 from contacting and damaging the walls and tissues of the hypopharynx.

If low-level, continuous suctioning is needed in stomach 50 and high-level, continuous suctioning is needed in the hypopharynx, then air source 622 can be inactivated while air source 640 continues to provide air to air tube 634. Similarly, if low-level, continuous suctioning is needed in hypopharynx region 40 and high-level, continuous suctioning is needed in stomach 50, then air source 622 is activated and air source 640 is inactivated.

In another embodiment, nasogastric tube structure 610 is configured so that suction tube 612, air tube 614 and end portion 616 are integral with each other. Similarly, in another embodiment, oropharyngeal tube structure 630 is configured so that suction tube 632, air tube 634 and end portion 636 are integral with each other. In a further embodiment, nasogastric tube structure 610 is configured so that the air tube (e.g. air tube 614) is positioned inside the suction tube (e.g. suction tube 612). Similarly, in a further embodiment, oropharyngeal tube structure 630 is configured so that its air tube (e.g. air tube 634) is positioned within the suction tube (e.g. suction tube 632).

Figure 11:
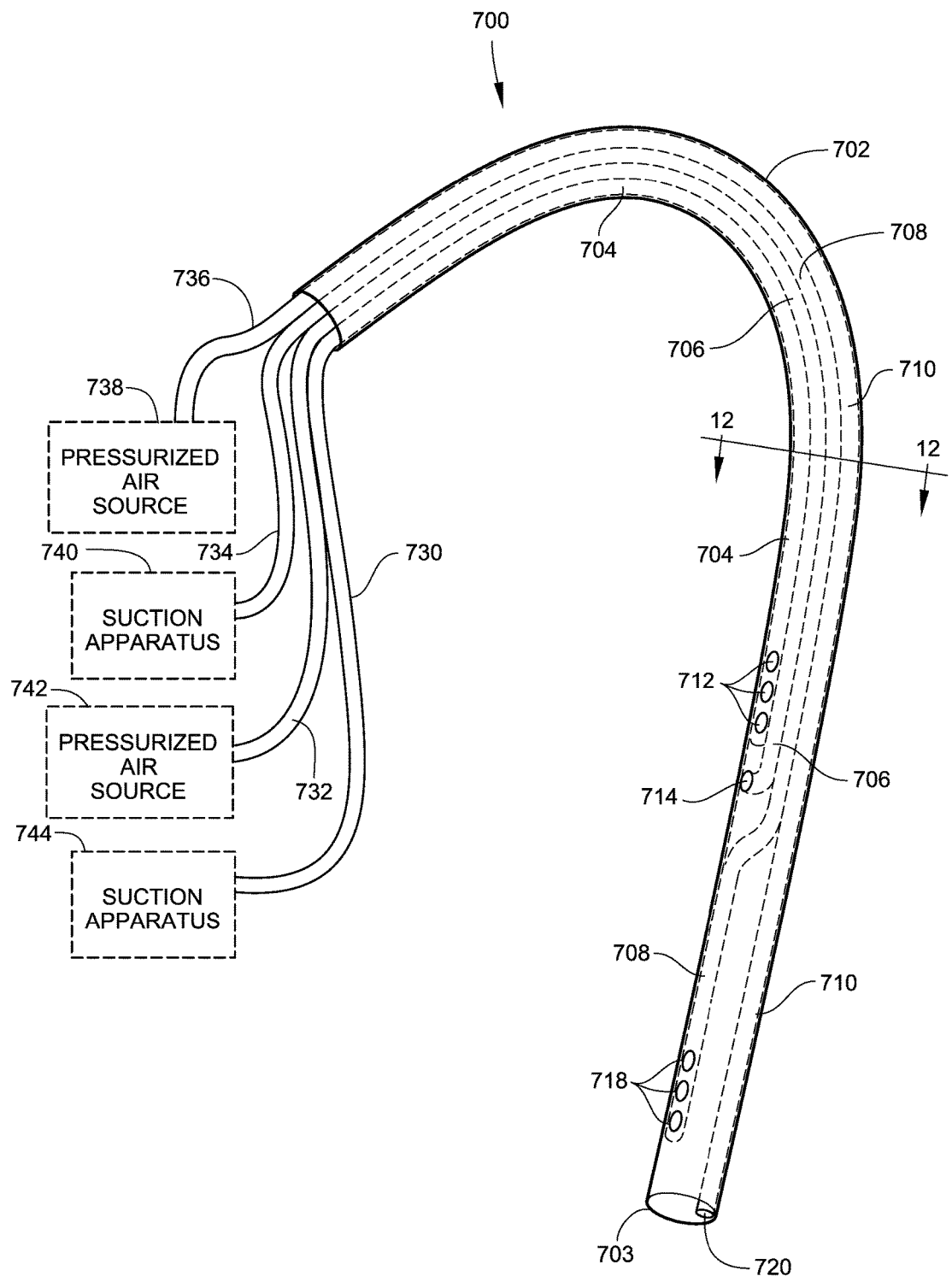
FIG. 11 is an elevational view of a medical apparatus in accordance with another embodiment of the invention.
Figure 12:
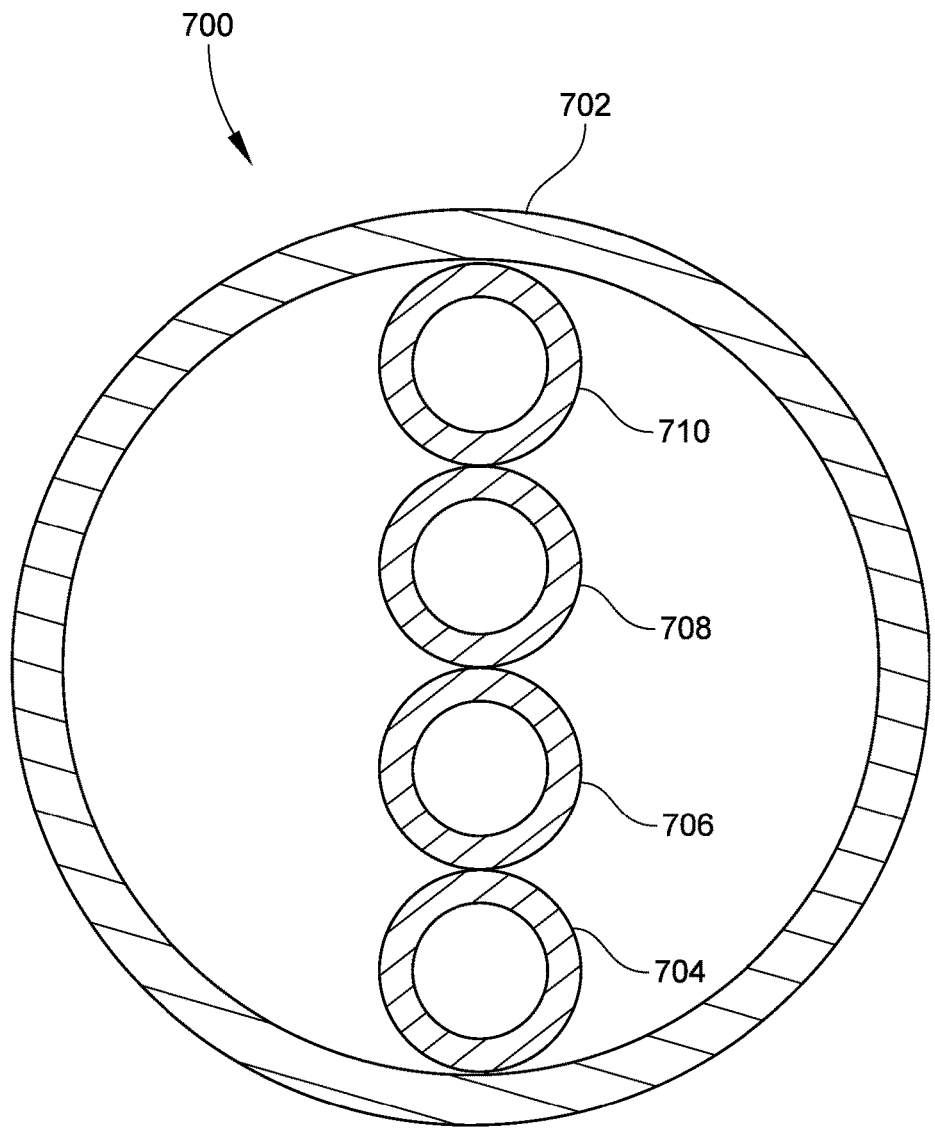
FIG. 12 is a cross-sectional view taken along line 12-12 in FIG. 11.
Figure 13:
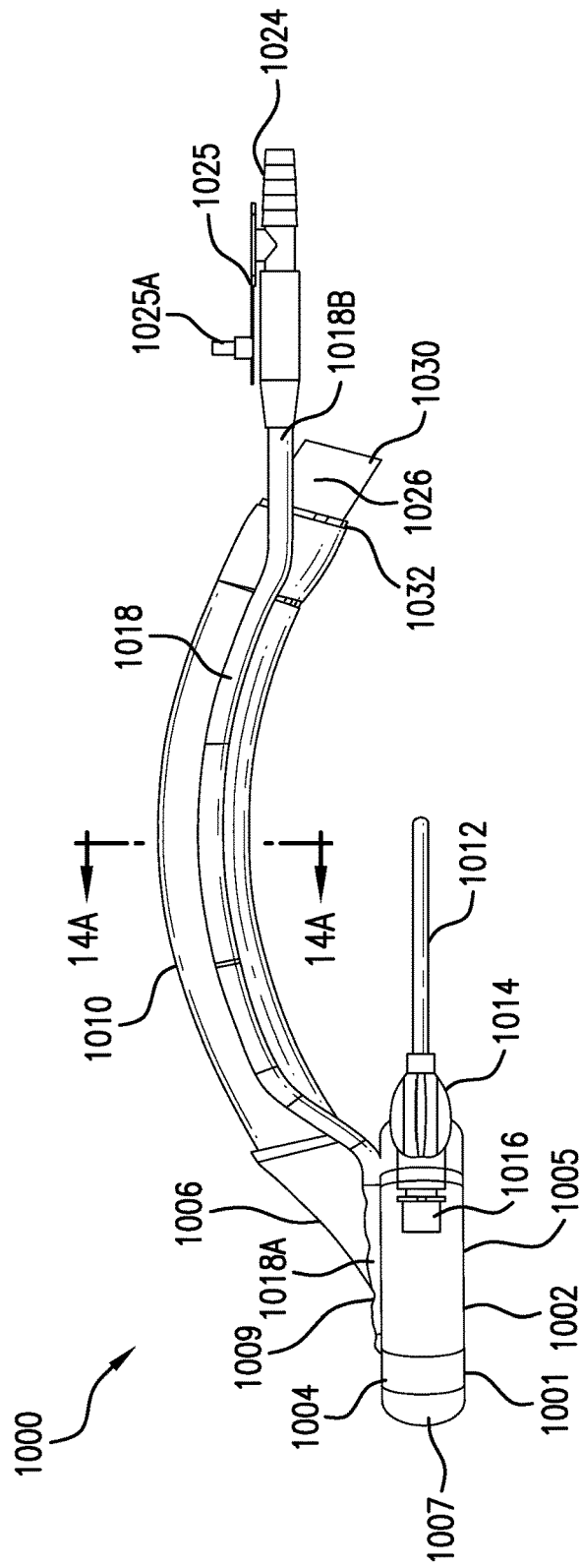
FIG. 13 is side view of a laryngeal mask apparatus in accordance with another embodiment of the invention.

Referring to FIGS. 11 and 12, there is shown medical apparatus 700 in accordance with another embodiment of the invention. As with medical apparatus 600, medical apparatus 700 is configured for use in the situation wherein continuous high-level suctioning is necessary. As will be shown by the ensuing discussion, medical apparatus 700 prevents collapse of the hypopharynx and stomach walls while continuous suctioning is occurring and also prevents damage to stomach and hypopharynx tissues. Medical apparatus 700 comprises outer tube 702 which is configured to be inserted either through a patient's mouth or patient's nose. Tube 702 has a distal end 703 and a predetermined length that allows end 703 to be positioned in a patient's stomach. Tube 702 comprises four separate conduits 704, 706, 708 and 710 which are not in communication with each other. Conduits 704 and 708 are suction conduits. Conduits 706 and 710 are air conduits. Tube 702 includes suction intakes or openings 712 that are in communication with suction conduit 704. Suction intakes 712 are located a predetermined location along the length of tube 702 that correlates to the hypopharynx region of a patient when tube 702 is inserted in a patient. When suction is applied to suction conduit 704, microaspirations and regurgitated material in the hypopharynx region are sucked through suction intakes 712 and up through conduit 704 and into an external suction apparatus as will be explained in the ensuing description. Tube 702 includes an opening or vent 714. Air conduit 706 is in communication with opening 714. When pressurized air is provided to air conduit 706, such air is vented through opening 714. The purpose of this configuration is explained in the ensuing discussion. Tube 702 also includes suction intakes or openings 718. Suction conduit 708 is in communication with suction intakes 718. When suction is applied to suction conduit 708, stomach contents are sucked through suction intakes 718 and up through suction conduit 708 and into an external suction apparatus as will be explained in the ensuing description. As shown in FIG. 11, air conduit 710 has opening or vent 720. When pressurized air is supplied to air conduit 710, the pressurized air vents through opening 720 and into the patient's stomach.

Referring to FIG. 11, medical apparatus 700 further comprises tube sections 730, 732, 734 and 736. Tube section 730 is joined to and in communication with conduit 704. Tube section 732 is joined to and in communication with conduit 706. Tube section 734 is joined to and in communication with conduit 708. Tube section 736 is joined to and in communication with conduit 710. Tube section 730 is configured to be connected to suction apparatus 744. Tube section 732 is configured to be connected to pressurized air source 742. Tube section 734 is configured to be connected to suction apparatus 740. Tube section 736 is configured to be connected to pressurized air source 738. Suction apparatuses 740 and 744 are separate apparatuses. In one scenario, one suction apparatus can provide high-level suction while the other suction apparatus can provide low-level suction. In another scenario, both suction apparatuses provide low-level suction. In a further scenario, both suction apparatuses provide high-level suction. Pressurized air sources 738 and 742 are separate air sources and each has an activated state and an inactivated state. Therefore, both pressurized air sources can be activated or inactivated or one pressurized source activated and the other pressurized air source inactivated.

When tube 702 is inserted into a patient and high-level suction of the stomach and hypopharynx is necessary, suction apparatuses 744 and 740 produce suction within suction conduits 704 and 708, respectively. Stomach contents are sucked into suction intakes 718, and microaspirations and regurgitated material in the hypopharynx region are sucked into suction intakes 712. All material sucked into suction intakes 712 and 718 are sucked through conduits 704 and 708, respectively, and into baskets or other containers inside suction apparatuses 744 and 740, respectively. In order to prevent suction intakes 712 and 718 from damaging tissues in the hypopharynx and stomach, respectively, pressurized air sources 742 and 738 provide air to air conduits 706 and 710, respectively. The pressurized air supplied to air conduit 706 is vented through opening 714 and the pressurized air provided to air conduit 710 is vented through opening 720. As a result, the pressurized air vented through opening 714 keeps suction intakes 712 away from hypopharynx tissue, and the pressurized air vented through opening 720 keeps suction intakes 718 away from stomach tissue. If high-level suctioning is needed in the hypopharynx but only low-level suctioning is needed in the stomach, then pressurized air source 738 can be inactivated while pressurized air source 742 remains activated. Similarly, if low-level suctioning is needed in the hypopharynx but high-level suctioning is needed in the stomach, then pressurized air source 742 can be inactivated while pressurized air source 738 remains activated.

In one embodiment, each conduit 704, 706, 708 and 710 is configured as a tube. In another embodiment, conduits 704, 706, 708 and 710 are integrally formed with tube 702 during the manufacturing process.

In one embodiment, tube 702 and conduits 704, 706, 708 and 710 are fabricated from the same materials used to fabricate the tubes of the medical apparatuses described in the foregoing description.

Referring to FIGS. 13, 14A, 15 and 16-24, there is shown laryngeal mask apparatus 1000 in accordance with a further embodiment of the invention. Laryngeal mask apparatus 1000 also suctions secretions and fluids in a patient's hypopharynx region. Laryngeal mask apparatus 1000 comprises mask or cuff portion 1001. Mask or cuff portion 1001 comprises front side 1002, rear side 1004 and inflatable tubular ring portion 1005. Joint section 1006 is joined or attached to rear side 1004 of mask 1001. In one embodiment, joint section 1006 has a generally tubular shape. Laryngeal mask apparatus 1000 comprises flexible breathing tube 1010 which is connected to joint section 1006. Flexible breathing tube 1010 has interior region 1011 for the flow of air and is discussed in detail in the ensuing description. The air in flexible breathing tube 1010 flows through the flexible breathing tube 1010 and through joint section 1006 and into mask 1001. Mask portion 1001 has end 1007.

Figure 14A:
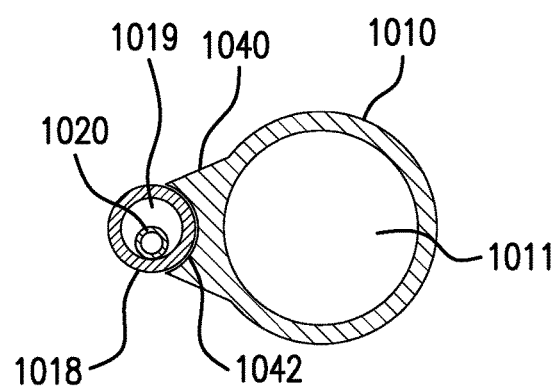
FIG. 14A is cross-sectional view taken along line 14A-14A in FIG. 13.
Figure 15:
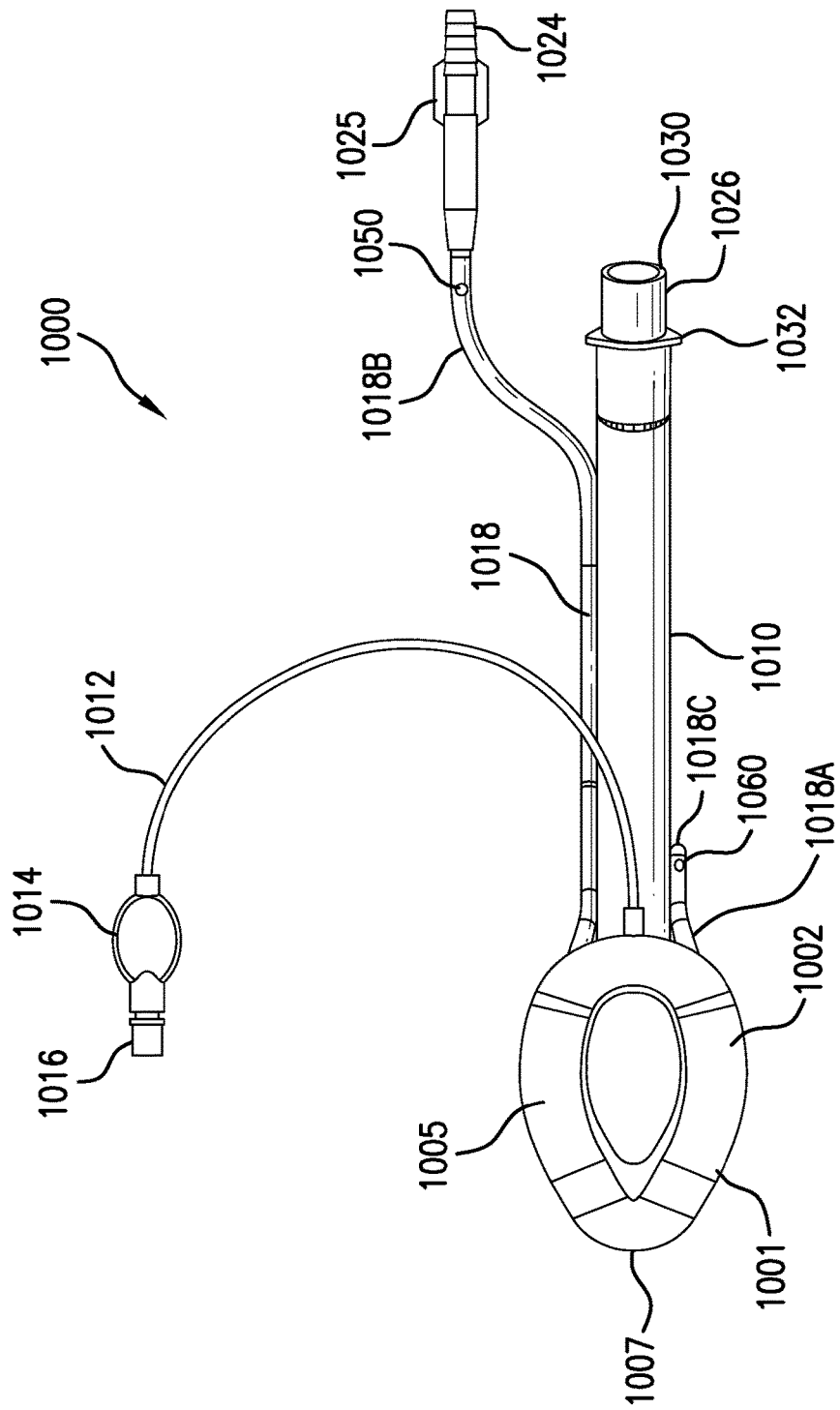
FIG. 15 is a bottom view of the laryngeal mask apparatus.
Figure 19:
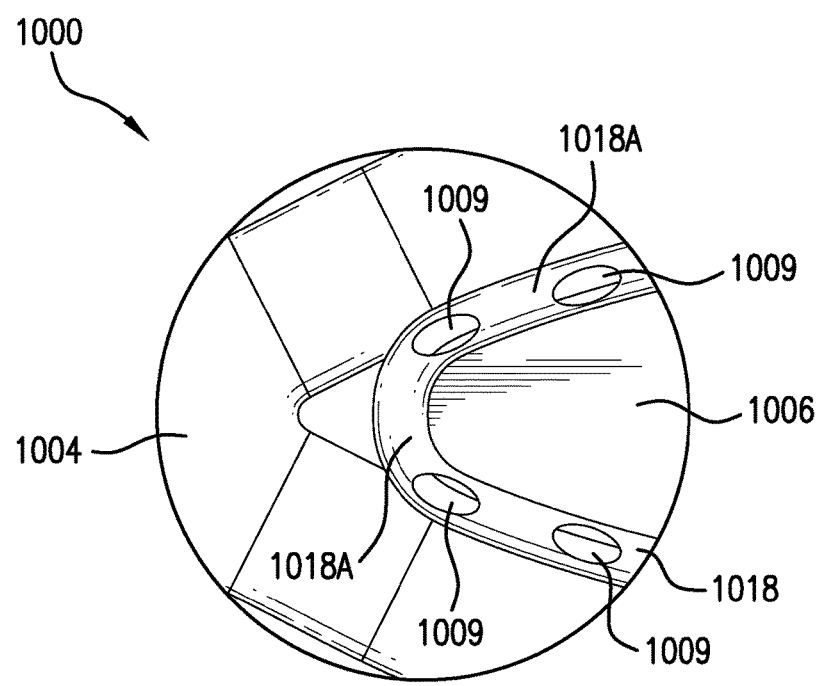
FIG. 19 is an enlarged view of a portion of the view of FIG. 18.
Figure 20:
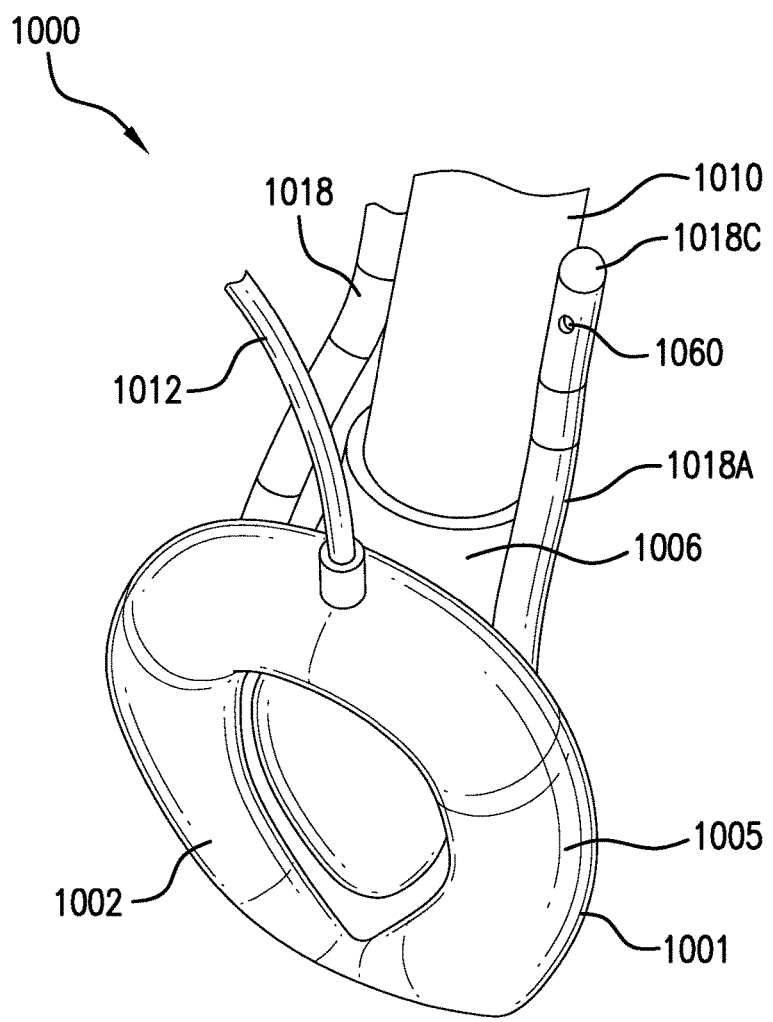
FIG. 20 is a perspective view of the front side of the mask portion of the laryngeal mask apparatus.
Figure 21:
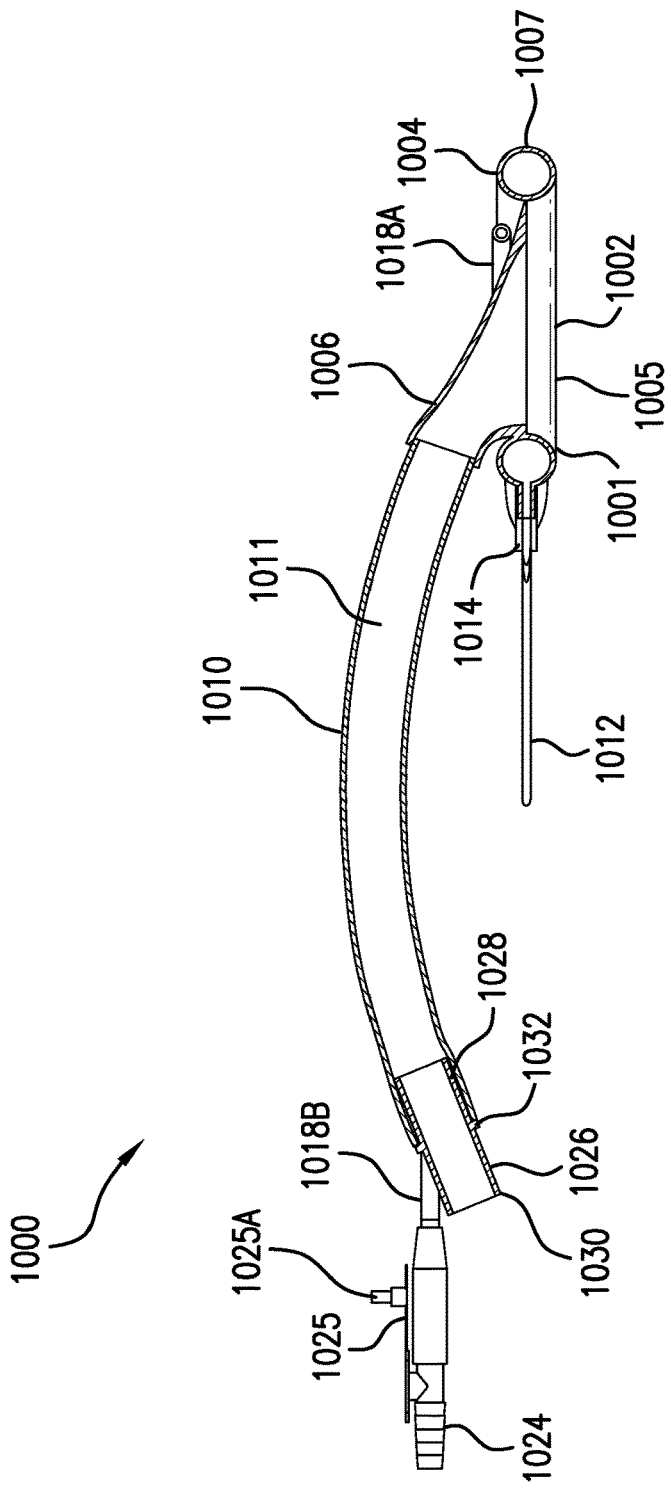
FIG. 21 is a cross-sectional view taken along line 21-21 of FIG. 17.
Figure 22:
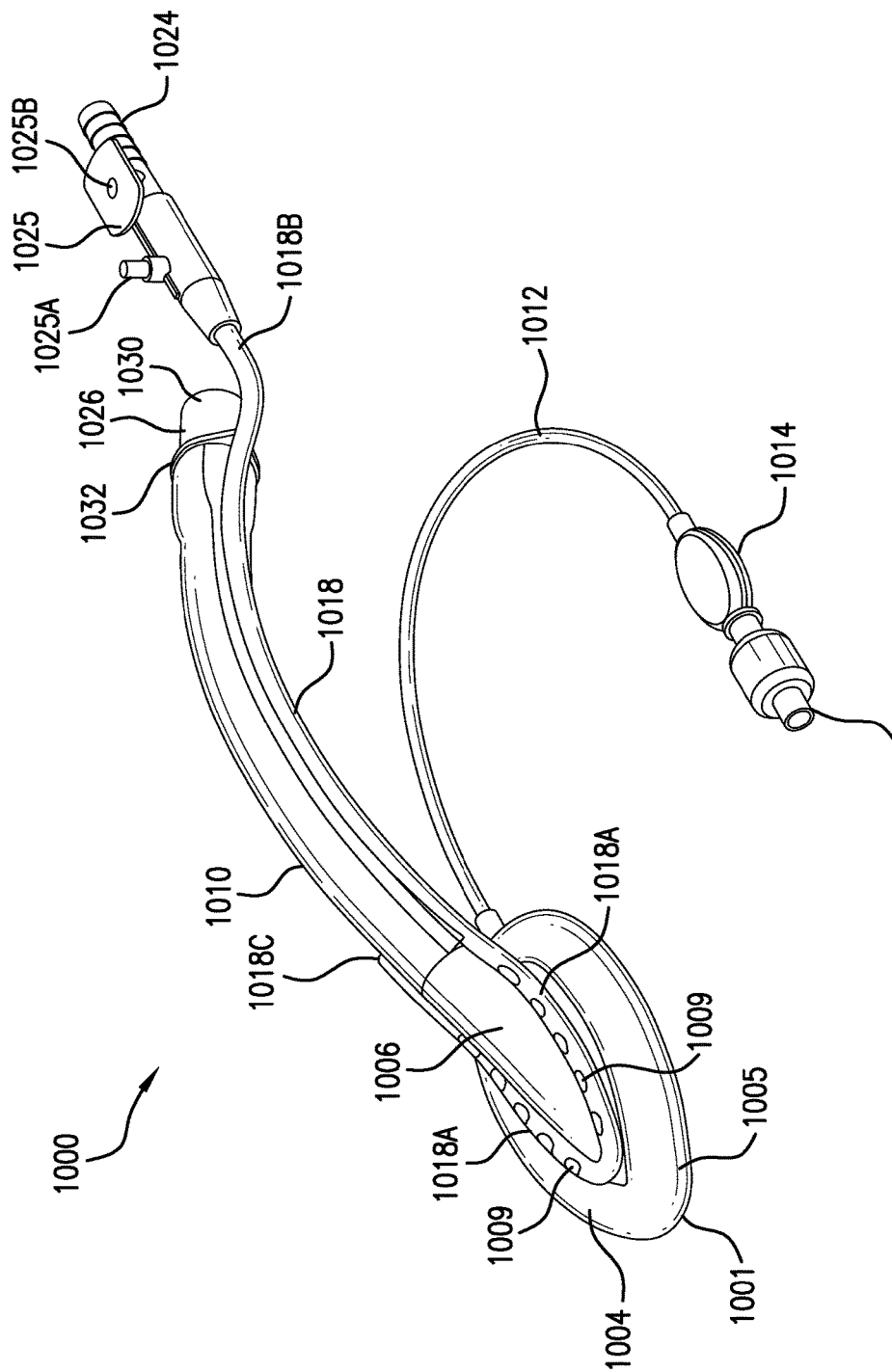
FIG. 22 is a perspective view of the laryngeal mask apparatus.
Figure 23:
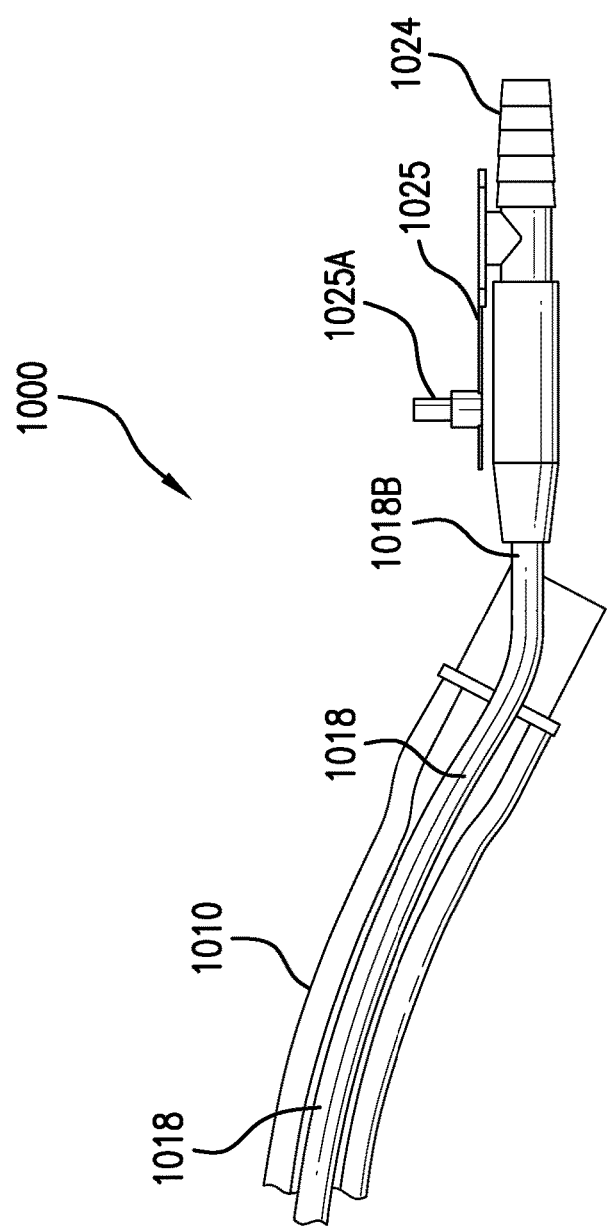
FIG. 23 is a side view of the suction connector depicted in FIG. 13.
Figure 24:
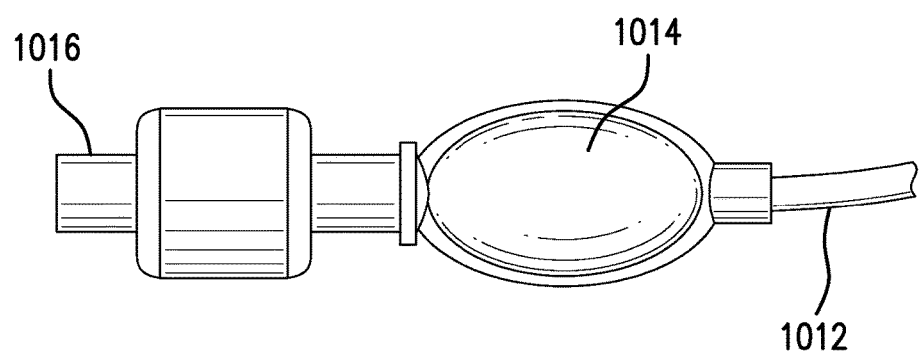
FIG. 24 is an enlarged, side view of a pilot valve and connector depicted in FIGS. 15, 18 and 22.

Laryngeal mask apparatus 1000 further comprises flexible tube 1018 that is joined or attached to the exterior surface of flexible breathing tube 1010 and extends to mask 1001. Flexible tube 1018 comprises portion 1018A. A substantial portion of portion 1018A is wrapped about and joined or attached to the exterior surface of joint section 1006. In another embodiment, the aforementioned substantial portion of portion 1018A is joined or attached to both the exterior surface of joint section 1006 and the rear side 1004 of mask portion 1001. In a further embodiment, the aforementioned substantial portion of portion 1018A is joined or attached to rear side 1004 and positioned or wrapped about joint section 1006. Portion 1018A of tube 1018 has a plurality of suction ports or openings 1009. Suction ports 1009 suck in the fluids and secretions in the patient's hypopharyngeal region as will be discussed in the ensuing description. Suction ports or openings 1009 are also shown in FIG. 19. FIG. 19 is an enlarged view of the portion of the view of FIG. 18 that is encompassed by the dashed circle and indicated by the number 19. As shown in FIG. 14A, tube 1018 has interior 1019 which is used for suction. Suction ports or openings 1009 are in communication with interior 1019. Tube 1018 includes air hole 1060 that is in portion 1018A of tube 1018 and in proximity to distal end 1018C of tube 1018. Tube 1018 further includes air hole 1050 that is in portion 1018B of tube 1018. Air hole 1050 functions as an air entry hole and air hole 1060 functions as an air exit hole. As shown in FIG. 15, the section of portion 1018A that has distal end 1018C and air hole 1060 is not joined or attached to joint section 1006 or mask 1001, but instead, is spaced part from mask 1001. This configuration ensures that air hole 1060 is not blocked by any portion of mask 1001.

Figure 14C:
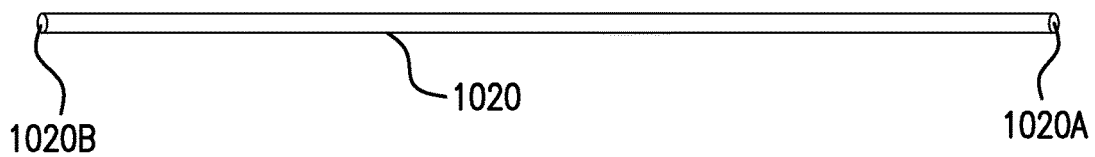
FIG. 14C is a view of a flexible air capillary tube that is shown in FIG. 14A.

Additional flexible tube 1018 further comprises flexible air capillary tube 1020 that is located within interior 1019 and extends for substantially the entire length of tube 1018. As shown in FIG. 14C, air capillary tube 1020 has first open end 1020A and opposite second open end 1020B. FIG. 14C shows air capillary tube 1020 in a straight configuration for purposes of facilitating understanding of the invention. However, it is to be understood that air capillary tube 1020 is flexible and will conform to the shape of additional flexible tube 1018. First open end 1020A of air capillary tube 1020 is in communication with air hole 1050. Opposite second open end 1020B of air capillary tube 1020 is in communication with the air hole 1060. When suction is created within interior 1019, the suction pressure draws air into air hole 1050. The air drawn into air hole 1050 enters first open end 1020A of air capillary tube 1020, flows through air capillary tube 1020, exits opposite second open end 1020B of air capillary tube 1020 and then exits air hole 1060. The air exiting air hole 1060 enters the patient's hypopharyngeal region so as to decrease the direct suction forces on the mucosa in the hypopharyngeal region. Thus, a sump function is created by: (a) the suction within interior 1019 of tube 1018 that draws air into air hole 1050 and into the first open end 1020A of air capillary tube 1020, (b) the flow of the air through the air capillary tube 1020, and (c) the flow of the air out of the second open end 1020B of air capillary tube 1020 and out of the air hole 1060.

In one embodiment, portion 1018A is configured so that air hole 1060 faces the front of the patient's throat. In another embodiment, portion 1018A is configured so that air hole 1060 faces the back of the patient's throat.

Suction tube connector 1024 is connected to portion 1018B of tube 1018. Thus, the interior of portion 1018B is in communication with the interior of suction tube connector 1024. Suction tube connector 1024 includes a suction enablement device 1025. Suction enablement device 1025 includes stop member 1025A and opening 1025B. Stop member 1025A is sized to be frictionally inserted into opening 1025B. Stop member 1025A must be inserted into opening 1025B in order for suction to take place through interior 1019 of tube 1018. Thus, if a suction producing device is connected to suction tube connector 1024, suction through interior 1019 will not occur unless stop member 1025A is plugged into opening 1025B. Such a configuration ensures that the patient's throat or mouth is not over-suctioned. The stop member 1025A is inserted into or removed from opening 1025B by medical personnel. When stop member 1025A is inserted into opening 1025B and a suction producing apparatus is connected to suction tube connector 1024, suction will be created throughout interior 1019 of tube 1018 which causes secretions and fluids to be sucked in through suction ports 1009. Suction within interior 1019 of tube 1018 causes air to be drawn into air hole 1050. As described in the foregoing description, the air that is drawn into the air hole 1050 then flows through air capillary tube 1020, exits air hole 1060 and then enters the area being suctioned so as to provide gentle but efficient suction without damaging the mucosa. Thus, the flow of air exiting air hole 1060 prevents suction ports 1009 from sticking to and sucking the mucosa. Such a configuration prevents trauma to and bleeding of the mucosa.

Figure 14B:
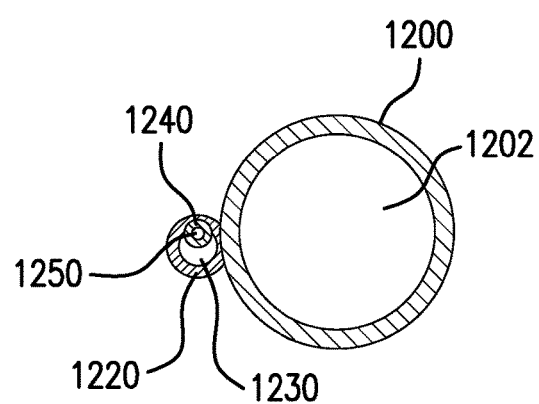
FIG. 14B is a cross-sectional view, similar to the view of FIG. 14A, of a flexible breathing tube and flexible tube structure in accordance with an alternate embodiment of the invention.

Referring to FIG. 14A, in one embodiment, flexible breathing tube 1010 is formed with a longitudinally extending protruding portion 1040 which has curved surface 1042. Tube 1018 is joined or attached to curved surface 1042 by any suitable technique, e.g. adhesive, heat treatment, etc. In another embodiment, tube 1018 is integrally formed with flexible breathing tube 1010. Referring to FIG. 14B, there is shown an alternate embodiment wherein flexible breathing tube 1010 and tube 1018 are replaced by flexible breathing tube 1200 and flexible tube 1220, respectively. Flexible breathing tube 1200 performs the same function as flexible breathing tube 1010 but has a different structure. Flexible breathing tube 1200 has interior 1202 and a substantially circular cross-section. Flexible tube 1220 performs the same function as tube 1018. Tube 1220 is joined or attached to the exterior surface of flexible breathing tube 1200 by any suitable technique, e.g. adhesive, heat treatment, etc. In one embodiment, tube 1220 is integrally formed with flexible breathing tube 1200. Tube 1220 has an interior 1230 which provides the same function as interior 1019 of tube 1018. Tube 1220 has air entry and air exit holes that perform the same functions as air holes 1050 and 1060, respectively. A flexible air capillary tube 1240 is positioned within tube 1220. Air capillary tube 1240 has the same structure and performs the same function as air capillary tube 1020. Air capillary tube 1240 has interior 1250.

Figure 16A:
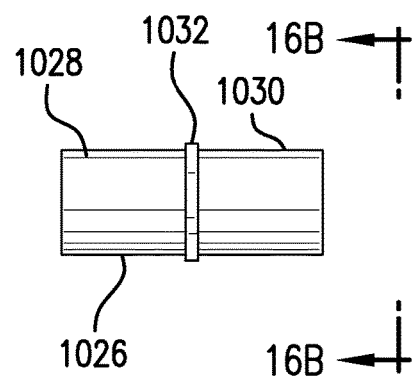
FIG. 16A is a side view of a mouthpiece shown in FIG. 15.
Figure 16B:
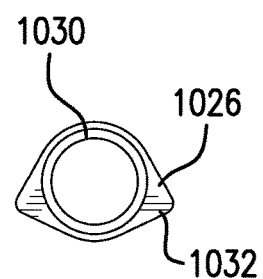
FIG. 16B is a view taken along line 16B-16B in FIG. 16A.
Figure 17:
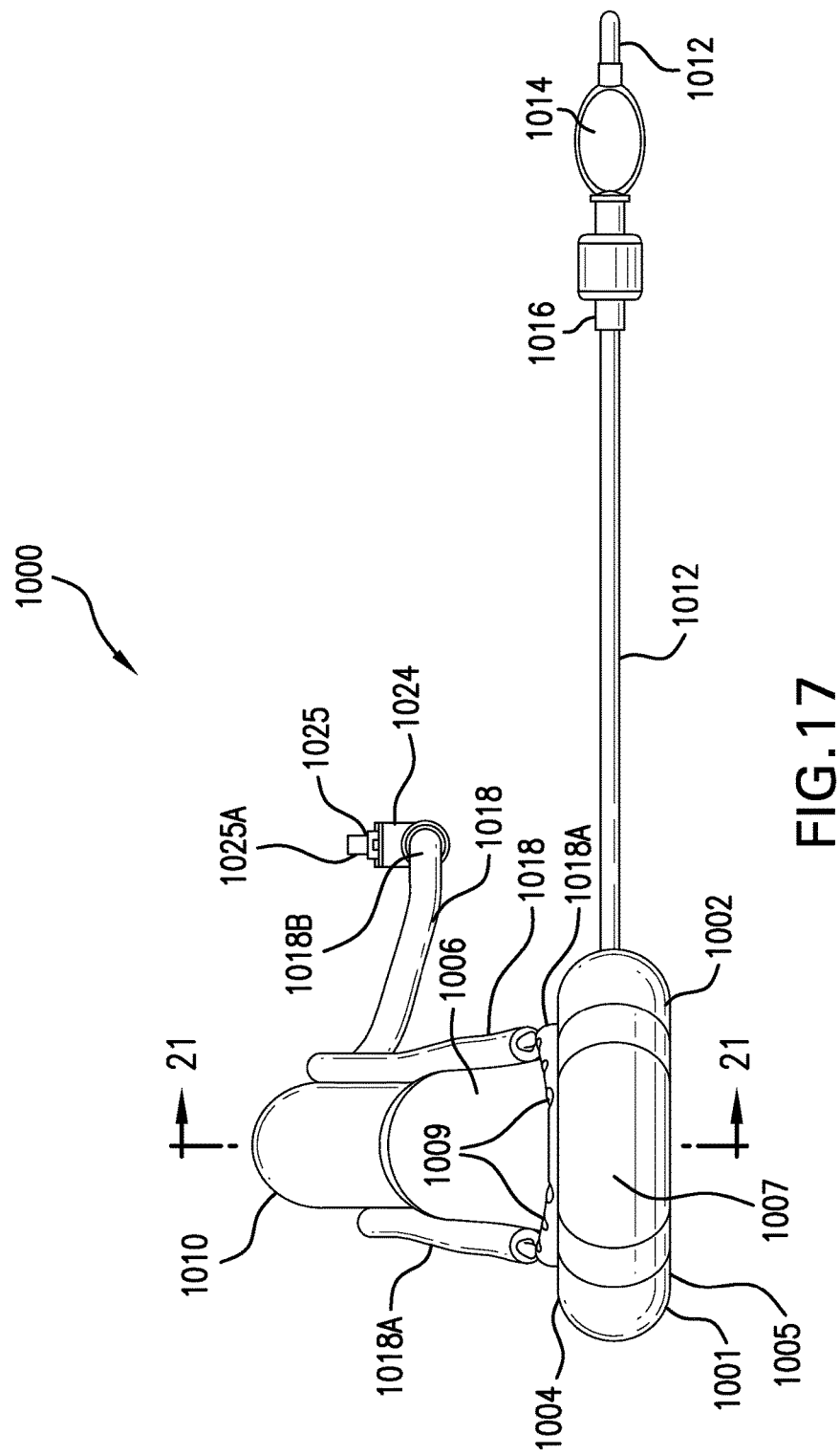
FIG. 17 is an end view of the laryngeal mask apparatus.
Figure 18:
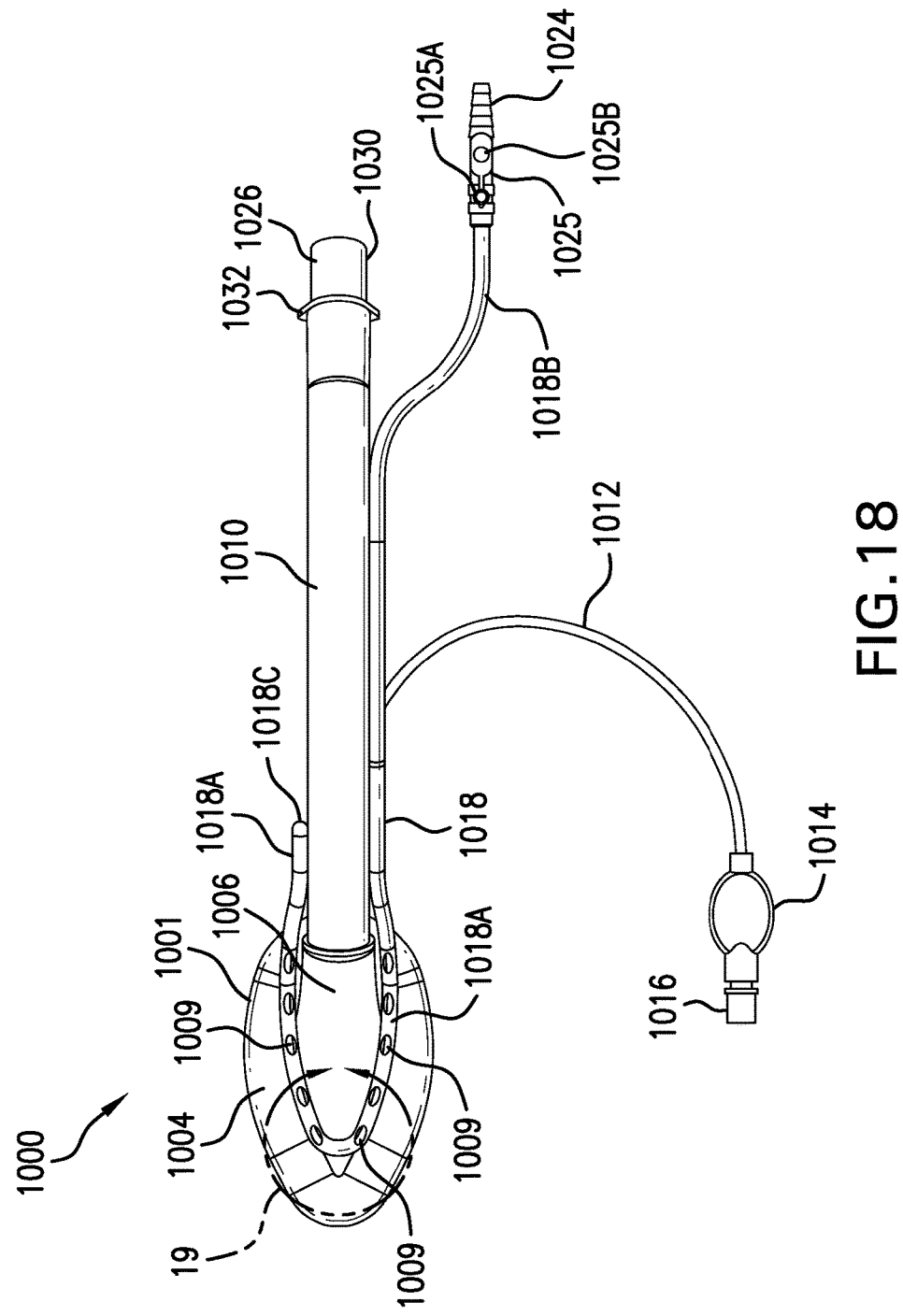
FIG. 18 is a top view of the laryngeal mask apparatus.

Referring to FIGS. 15 and 16, laryngeal mask apparatus 1000 includes mouthpiece connector 1026 that is configured to be connected to a ventilating system which provides air, oxygen and anesthesia gases. Mouthpiece 1026 comprises portion 1028 that is configured and sized to be frictionally inserted into the opening of flexible breathing tube 1010. Mouthpiece 1026 further comprises portion 1030 that is configured to be connected to the ventilating system. Mouthpiece 1026 further comprises flange portion 1032 that separates portions 1028 and 1030 and abuts the end of flexible breathing tube 1010 when portion 1028 is completely inserted into the opening of the flexible breathing tube 1010.

Referring to FIGS. 15, 17, 18 and 24, laryngeal mask apparatus 1000 further comprises air tube 1012 that is connected to mask 1001. Laryngeal mask apparatus 1000 further comprises pilot valve 1014 which is connected to air tube 1012, and connector 1016 that is connected to pilot valve 1014. Connector 1016 is configured to be connected to an air source which provides an air stream that inflates tubular ring 1005 of mask portion 1001. The pilot valve 1014 controls the amount of air that passes through air tube 1012 and into tubular ring 1005.

When in use, laryngeal mask apparatus 1000 is inserted into the patient's mouth and down through the patient's throat past the epiglottis until mask portion 1001 comes to rest with end 1007 of mask portion 1001 positioned in the base of the patient's throat, lying against the upper end of the normally closed esophagus. Suction ports 1009 face the back of the throat. Inflatable ring 1005 is then inflated via air tube 1012 and valve 1014 to seal the area around the inlet to the larynx. The patient's airway is thus secure and unobstructed and flexible breathing tube 1010 is then connected directly to the conventional anesthetic circuit hosing for either positive pressure or spontaneous breathing. Suction connector 1024 is then connected to a suction producing apparatus and stop member 1025A is inserted into opening 1025B to allow suction ports 1009 to suck oropharyngeal secretions from the mouth and the back of the patient's throat. Such secretions are made not only from the patient's stomach, but also from the salivary glands in the mouth. Air holes 1050 and 1060 of tube 1018 cooperate with air capillary tube 1020 to ensure that the suction at suction ports 1009 does not damage the mucosa.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A laryngeal mask apparatus (1000) for facilitating ventilation of a patient comprising:
   a mask (1001) comprising a front side (1002) and a rear side (1004) that faces a back of a patient's throat when the mask (1001) is positioned within the patient's throat, an inflatable tubular ring (1005), an air tube (1012) that is connected to the inflatable tubular ring (1005) and adapted to be connected to an air source to enable inflation of the inflatable tubular ring (1005);
   a joint section (1006) attached to the rear side (1004) of the mask (1001) and having an exterior surface;
   a flexible breathing tube (1010) connected to the joint section (1006), the flexible breathing tube (1010) having an interior (1011) to receive airflow therethrough, wherein air in the flexible breathing tube (1010) flows through the flexible breathing tube (1010) and through the joint section (1006) and into the mask (1001), the flexible breathing tube (1010) having a portion configured for connection to a ventilating system;
   an additional flexible tube (1018) having a length and comprising an interior (1019), a first portion (1018A) and a second portion (1018B) that is configured to be connected to a suction producing device that produces suction within the interior (1019) of the additional flexible tube (1018), wherein a substantial portion of the first portion (1018A) is wrapped about and attached to the exterior surface of the joint section (1006), wherein the additional flexible tube (1018) extends to a distal end (1018C) which is part of the first portion (1018A), the first portion (1018A) having a plurality of suction ports (1009) in communication with the interior (1019), the plurality of suction ports (1009) being located in the first portion (1018A) such that the plurality of suction ports (1009) face the back of the patient's throat when the mask (1001) is positioned within the patient's throat so that the plurality of suction ports (1009) suck in fluids and secretions in the patient's hypopharyngeal region when suction is created within the interior (1019), the additional flexible tube (1018) further comprising an air entry hole (1050) in the second portion (1018B) and an air exit hole (1060) in the first portion (1018A), wherein the distal end (1018C) and the air exit hole (1060) are spaced apart from the mask (1001); and wherein the additional flexible tube (1018) further comprises a flexible air capillary tube (1020) that is positioned within the interior (1019) of the additional flexible tube (1018) and the flexible air capillary tube (1020) extends for substantially all of the length of the additional flexible tube (1018), the flexible air capillary tube (1020) having a first open end (1020A) in communication with the air entry hole (1050) and an opposite second open end (1020B) in communication with the air exit hole (1060), wherein when suction is created within the interior (1019), air is drawn into the air entry hole (1050) and enters the first open end (1020A) of the flexible air capillary tube (1020) wherein the air then flows through the flexible air capillary tube (1020), exits the second open end (1020B) and then exits the air exit hole (1060), such that when the mask (1001) is positioned within the patient's throat and suction is created within the interior (1019), the air exiting the air exit hole (1060) decreases direct suction forces on mucosa of the patient's throat that are caused by the suction of the plurality of suction ports (1009).

2. The laryngeal mask apparatus (1000) according to claim 1, wherein the first portion (1018A) is also attached to the rear side (1004) of the mask (1001).

3. The laryngeal mask apparatus (1000) according to claim 1, wherein the additional flexible tube (1018) has a middle portion that is between the first portion (1018A) and the second portion (1018B), the middle portion being joined or attached to the flexible breathing tube (1010).

4. The laryngeal mask apparatus (1000) according to claim 1, further comprising a suction tube connector (1024) that is connected to the second portion (1018B) of the additional flexible tube (1018).

5. The laryngeal mask apparatus (1000) according to claim 4, wherein the suction tube connector (1024) is adapted to be connected to the suction producing device.

6. The laryngeal mask apparatus (1000) according to claim 1, further comprising a connector (1026) that has a first portion (1028) configured for insertion into the flexible breathing tube (1010) and a second portion (1030) that is configured for connection to the ventilating system.

* * * * *